(12) United States Patent
Rafiee et al.

(10) Patent No.: US 12,376,956 B2
(45) Date of Patent: Aug. 5, 2025

(54) PERCUTANEOUS SHUNT DEVICES AND RELATED METHODS

(71) Applicant: Transmural Systems LLC, Andover, MA (US)

(72) Inventors: Nasser Rafiee, Andover, MA (US); Stuart MacDonald, Andover, MA (US); Koosha Rafiee, Andover, MA (US); Mai Le Diep, Andover, MA (US)

(73) Assignee: Transmural Systems LLC, Andover, MA (US)

( * ) Notice: Subject to any disclaimer, the term of this patent is extended or adjusted under 35 U.S.C. 154(b) by 430 days.

(21) Appl. No.: 16/264,402

(22) Filed: Jan. 31, 2019

(65) Prior Publication Data

US 2019/0231510 A1    Aug. 1, 2019

Related U.S. Application Data

(63) Continuation-in-part of application No. PCT/US2018/049373, filed on Sep. 4, 2018.
(Continued)

(51) Int. Cl.
*A61F 2/07* (2013.01)
*A61B 17/11* (2006.01)
(Continued)

(52) U.S. Cl.
CPC .............. *A61F 2/064* (2013.01); *A61B 17/11* (2013.01); *A61F 2/07* (2013.01); *A61F 2/958* (2013.01); *A61L 27/507* (2013.01); *A61L 31/06* (2013.01); *A61M 27/002* (2013.01); *A61B 2017/1107* (2013.01); *A61B 2017/1139* (2013.01); *A61F 2002/821* (2013.01); *A61F 2250/0029* (2013.01); *A61F 2250/0039* (2013.01); *A61F 2250/0082* (2013.01); *A61F 2250/0098* (2013.01); *A61M 25/10* (2013.01); *A61M 2025/1081* (2013.01)

(58) Field of Classification Search
CPC .................................................. A61F 2002/821
See application file for complete search history.

(56) References Cited

U.S. PATENT DOCUMENTS

| 4,106,129 A | 8/1978 | Carpentier et al. |
| 4,259,753 A | 4/1981 | Liotta et al. |

(Continued)

FOREIGN PATENT DOCUMENTS

| EP | 2421468 | 10/2010 |
| EP | 2412397 A1 | 2/2012 |

(Continued)

OTHER PUBLICATIONS

International Search Report, for related application No. PCT/US2011/059586, mailed May 25, 2012.
(Continued)

*Primary Examiner* — Jacqueline Woznicki
(74) *Attorney, Agent, or Firm* — DeWitt LLP; Brian R. Pollack, Esq.

(57) ABSTRACT

The disclosure provides various embodiments of prostheses and delivery systems to permit an interventional cardiologist to create shunts between various blood vessels. Moreover, the disclosed shunts can be used to shunt between various hollow organs, as set forth in the present disclosure.

14 Claims, 16 Drawing Sheets

Related U.S. Application Data

(60) Provisional application No. 62/664,722, filed on Apr. 30, 2018, provisional application No. 62/615,330, filed on Jan. 9, 2018, provisional application No. 62/615,433, filed on Jan. 9, 2018, provisional application No. 62/553,532, filed on Sep. 1, 2017.

(51) Int. Cl.

| | |
|---|---|
| *A61F 2/06* | (2013.01) |
| *A61F 2/82* | (2013.01) |
| *A61F 2/958* | (2013.01) |
| *A61L 27/50* | (2006.01) |
| *A61L 31/06* | (2006.01) |
| *A61M 27/00* | (2006.01) |
| *A61M 25/10* | (2013.01) |

(56) References Cited

U.S. PATENT DOCUMENTS

| | | | |
|---|---|---|---|
| 4,666,442 A | 5/1987 | Arru et al. | |
| 4,692,164 A | 9/1987 | Dzemeshkevich et al. | |
| 5,411,552 A | 5/1995 | Andersen et al. | |
| 5,449,384 A | 9/1995 | Johnson | |
| 5,606,928 A | 3/1997 | Religa et al. | |
| 5,607,444 A * | 3/1997 | Lam | A61F 2/954 604/104 |
| 5,639,278 A | 6/1997 | Dereume et al. | |
| 5,749,921 A | 5/1998 | Lenker et al. | |
| 5,788,715 A | 8/1998 | Watson, Jr. et al. | |
| 5,861,028 A | 1/1999 | Angell | |
| 5,895,410 A | 4/1999 | Forber et al. | |
| 5,928,281 A | 7/1999 | Huynh et al. | |
| 6,059,769 A | 5/2000 | Lunn et al. | |
| 6,074,416 A * | 6/2000 | Berg | A61F 2/07 623/1.36 |
| 6,096,071 A * | 8/2000 | Yadav | A61F 2/91 606/195 |
| 6,106,510 A | 8/2000 | Lunn et al. | |
| 6,152,937 A * | 11/2000 | Peterson | A61F 2/88 606/153 |
| 6,238,430 B1 | 5/2001 | Klumb et al. | |
| 6,375,774 B1 | 4/2002 | Lunn et al. | |
| 6,468,303 B1 * | 10/2002 | Amplatz | A61B 17/11 623/1.2 |
| 6,582,463 B1 * | 6/2003 | Mowry | A61F 2/06 623/1.1 |
| 6,599,303 B1 | 7/2003 | Peterson | |
| 6,602,271 B2 | 8/2003 | Adams et al. | |
| 6,616,675 B1 * | 9/2003 | Evard | A61B 18/1445 606/155 |
| 6,716,231 B1 | 4/2004 | Rafiee et al. | |
| 6,733,525 B2 | 5/2004 | Yang et al. | |
| 6,790,229 B1 | 9/2004 | Berreklouw | |
| 6,797,000 B2 | 9/2004 | Simpson et al. | |
| 6,800,081 B2 | 10/2004 | Parodi | |
| 6,866,677 B2 | 3/2005 | Douk et al. | |
| 6,911,036 B2 | 6/2005 | Douk et al. | |
| 6,926,690 B2 | 8/2005 | Renati | |
| 6,953,476 B1 | 10/2005 | Shalev | |
| 6,960,217 B2 | 11/2005 | Bolduc | |
| 7,044,958 B2 | 5/2006 | Douk et al. | |
| 7,066,946 B2 | 6/2006 | Douk et al. | |
| 7,182,771 B1 * | 2/2007 | Houser | A61B 17/11 623/1.36 |
| 7,189,259 B2 | 3/2007 | Simionescu et al. | |
| 7,195,641 B2 | 3/2007 | Palmaz et al. | |
| 7,201,772 B2 | 4/2007 | Schwammenthal et al. | |
| 7,294,135 B2 | 11/2007 | Stephens et al. | |
| 7,316,706 B2 | 1/2008 | Bloom et al. | |
| 7,399,315 B2 | 7/2008 | Iobbi | |
| 7,425,219 B2 | 9/2008 | Quadri | |
| 7,442,204 B2 | 10/2008 | Schwammenthal et al. | |
| 7,442,207 B2 | 10/2008 | Rafiee | |
| 7,445,631 B2 | 11/2008 | Salahieh et al. | |
| 7,481,838 B2 | 1/2009 | Carpentier et al. | |
| 7,491,232 B2 | 2/2009 | Bolduc et al. | |
| 7,524,330 B2 | 4/2009 | Berreklouw | |
| 7,655,040 B2 | 2/2010 | Douk et al. | |
| 7,682,352 B2 | 3/2010 | Rafiee et al. | |
| 7,699,892 B2 | 4/2010 | Rafiee et al. | |
| 7,716,801 B2 | 5/2010 | Douk et al. | |
| 7,753,840 B2 | 7/2010 | Simionescu et al. | |
| 7,753,949 B2 | 7/2010 | Lamphere et al. | |
| 7,780,726 B2 | 8/2010 | Seguin | |
| 7,799,069 B2 | 9/2010 | Bailey et al. | |
| 7,806,917 B2 | 10/2010 | Xiao | |
| 7,806,919 B2 | 10/2010 | Bloom et al. | |
| 7,815,673 B2 | 10/2010 | Bloom et al. | |
| 7,947,072 B2 | 5/2011 | Yang et al. | |
| 7,955,384 B2 | 6/2011 | Rafiee et al. | |
| 7,972,370 B2 | 7/2011 | Douk et al. | |
| 7,998,188 B2 | 8/2011 | Zilla et al. | |
| 8,002,825 B2 | 8/2011 | Letac et al. | |
| 8,052,750 B2 | 11/2011 | Tuval et al. | |
| 8,062,355 B2 | 11/2011 | Figulla et al. | |
| 8,070,802 B2 | 12/2011 | Lamphere et al. | |
| 8,092,518 B2 | 1/2012 | Schreck | |
| 8,092,520 B2 | 1/2012 | Quadri | |
| 8,092,524 B2 | 1/2012 | Nugent et al. | |
| 8,226,710 B2 | 7/2012 | Nguyen et al. | |
| 8,252,051 B2 | 8/2012 | Chau et al. | |
| 8,308,798 B2 | 11/2012 | Pintor et al. | |
| 8,337,541 B2 | 12/2012 | Quadri et al. | |
| 8,343,029 B2 * | 1/2013 | Farnan | A61M 1/3666 607/101 |
| 8,348,995 B2 | 1/2013 | Tuval et al. | |
| 8,348,996 B2 | 1/2013 | Tuval et al. | |
| 8,353,954 B2 | 1/2013 | Cai et al. | |
| 8,353,955 B2 | 1/2013 | Styrc et al. | |
| 8,518,096 B2 | 8/2013 | Nelson | |
| 9,173,737 B2 * | 11/2015 | Hill | A61F 2/2457 |
| 9,463,269 B2 * | 10/2016 | Cully | A61B 17/11 |
| 9,549,817 B2 * | 1/2017 | Rafiee | A61F 2/2418 |
| 9,566,149 B2 * | 2/2017 | Shaw | A61F 2/07 |
| 10,433,851 B2 * | 10/2019 | Adams | A61B 17/0057 |
| 10,499,920 B2 * | 12/2019 | Hall | A61F 2/07 |
| 10,583,002 B2 * | 3/2020 | Lane | A61F 2/2436 |
| 10,617,542 B2 * | 4/2020 | Chakfe | A61F 2/90 |
| 2001/0021872 A1 | 9/2001 | Bailey et al. | |
| 2002/0032481 A1 | 3/2002 | Gabbay | |
| 2002/0138138 A1 | 9/2002 | Yang | |
| 2003/0055495 A1 | 3/2003 | Pease et al. | |
| 2003/0065386 A1 | 4/2003 | Weadock | |
| 2003/0097172 A1 | 5/2003 | Shalev et al. | |
| 2004/0087998 A1 | 5/2004 | Lee et al. | |
| 2004/0116945 A1 * | 6/2004 | Sharkawy | A61F 2/064 606/153 |
| 2004/0127916 A1 | 7/2004 | Bolduc et al. | |
| 2005/0038508 A1 | 2/2005 | Gabbay | |
| 2005/0043790 A1 | 2/2005 | Seguin | |
| 2005/0049675 A1 | 3/2005 | Wallace | |
| 2005/0055082 A1 | 3/2005 | Ben-Muvhar et al. | |
| 2005/0137769 A1 | 6/2005 | Salahieh et al. | |
| 2005/0143809 A1 | 6/2005 | Salahieh et al. | |
| 2005/0177180 A1 | 8/2005 | Kaganov et al. | |
| 2005/0222672 A1 * | 10/2005 | Shmulewitz | A61F 2/88 623/1.15 |
| 2005/0288706 A1 | 12/2005 | Widomski et al. | |
| 2006/0085012 A1 | 4/2006 | Dolan | |
| 2006/0106449 A1 | 5/2006 | Ben-Muvhar | |
| 2006/0106450 A1 | 5/2006 | Ben-Muvhar | |
| 2006/0155359 A1 * | 7/2006 | Watson | A61F 2/07 623/1.13 |
| 2006/0173537 A1 | 8/2006 | Yang et al. | |
| 2007/0043435 A1 | 2/2007 | Seguin et al. | |
| 2007/0055358 A1 * | 3/2007 | Krolik | A61F 2/915 623/1.31 |
| 2007/0067029 A1 | 3/2007 | Gabbay | |
| 2007/0073337 A1 * | 3/2007 | Abbott | A61B 17/0057 606/213 |
| 2007/0088425 A1 * | 4/2007 | Schaeffer | A61F 2/07 623/1.13 |

(56) References Cited

U.S. PATENT DOCUMENTS

| | | | |
|---|---|---|---|
| 2007/0088428 A1* | 4/2007 | Teichman | A61F 2/91 623/1.35 |
| 2007/0249985 A1* | 10/2007 | Brenneman | A61B 17/083 604/890.1 |
| 2007/0250160 A1 | 10/2007 | Rafiee | |
| 2007/0255398 A1 | 11/2007 | Yang et al. | |
| 2007/0288089 A1 | 12/2007 | Gurskis et al. | |
| 2007/0293942 A1 | 12/2007 | Mizraee | |
| 2008/0015687 A1 | 1/2008 | Lashinski et al. | |
| 2008/0021537 A1 | 1/2008 | Ben-Muvhar et al. | |
| 2008/0065191 A1 | 3/2008 | Bolduc et al. | |
| 2008/0065204 A1* | 3/2008 | Macoviak | A61F 2/2454 623/2.17 |
| 2008/0077234 A1 | 3/2008 | Styrc | |
| 2008/0125860 A1 | 5/2008 | Webler et al. | |
| 2008/0208328 A1 | 8/2008 | Antocci et al. | |
| 2008/0221672 A1 | 9/2008 | Lamphere et al. | |
| 2008/0228256 A1* | 9/2008 | Erickson | A61F 2/064 623/1.11 |
| 2009/0005863 A1 | 1/2009 | Goetz et al. | |
| 2009/0062841 A1 | 3/2009 | Amplatz et al. | |
| 2009/0177262 A1* | 7/2009 | Oberti | A61F 2/90 623/1.36 |
| 2009/0234435 A1* | 9/2009 | Johnson | A61F 2/86 623/1.36 |
| 2009/0234436 A1* | 9/2009 | Johnson | A61F 2/86 623/1.36 |
| 2009/0234437 A1* | 9/2009 | Johnson | A61F 2/954 623/1.36 |
| 2009/0248133 A1* | 10/2009 | Bloom | A61F 2/91 623/1.15 |
| 2009/0270966 A1 | 10/2009 | Douk et al. | |
| 2009/0270976 A1 | 10/2009 | Douk et al. | |
| 2009/0306768 A1 | 12/2009 | Quadri | |
| 2009/0319038 A1 | 12/2009 | Gurskis et al. | |
| 2010/0036401 A1* | 2/2010 | Navia | A61F 2/064 606/155 |
| 2010/0036479 A1 | 2/2010 | Hill et al. | |
| 2010/0049306 A1* | 2/2010 | House | A61F 2/2418 623/1.26 |
| 2010/0082094 A1 | 4/2010 | Quadri et al. | |
| 2010/0100167 A1 | 4/2010 | Bortlein et al. | |
| 2010/0160847 A1 | 6/2010 | Braido et al. | |
| 2010/0174363 A1 | 7/2010 | Castro | |
| 2010/0179648 A1 | 7/2010 | Richter et al. | |
| 2010/0179649 A1 | 7/2010 | Richter et al. | |
| 2010/0185275 A1 | 7/2010 | Richter et al. | |
| 2010/0241218 A1* | 9/2010 | Bruszewski | D04C 1/06 623/1.28 |
| 2010/0249923 A1 | 9/2010 | Alkhatib et al. | |
| 2010/0262232 A1 | 10/2010 | Annest | |
| 2010/0280606 A1 | 11/2010 | Naor | |
| 2010/0298931 A1 | 11/2010 | Quadri et al. | |
| 2010/0312326 A1 | 12/2010 | Chuter et al. | |
| 2011/0112632 A1 | 5/2011 | Chau et al. | |
| 2011/0137409 A1 | 6/2011 | Yang et al. | |
| 2011/0172784 A1 | 7/2011 | Richter et al. | |
| 2011/0257723 A1* | 10/2011 | McNamara | A61F 2/2493 623/1.11 |
| 2011/0282438 A1 | 11/2011 | Drews et al. | |
| 2011/0306916 A1* | 12/2011 | Nitzan | A61F 2/2412 604/9 |
| 2011/0313515 A1 | 12/2011 | Quadri et al. | |
| 2011/0319988 A1 | 12/2011 | Schankereli et al. | |
| 2011/0319989 A1 | 12/2011 | Lane et al. | |
| 2012/0022639 A1 | 1/2012 | Hacohen | |
| 2012/0053686 A1* | 3/2012 | McNamara | A61B 17/0057 623/2.36 |
| 2012/0059450 A1 | 3/2012 | Chiang et al. | |
| 2012/0065652 A1 | 3/2012 | Cully et al. | |
| 2012/0078353 A1 | 3/2012 | Quadri et al. | |
| 2012/0078360 A1 | 3/2012 | Rafiee | |
| 2012/0143141 A1* | 6/2012 | Verkaik | A61M 60/00 604/175 |
| 2012/0179244 A1 | 7/2012 | Schankereli et al. | |
| 2012/0215303 A1 | 8/2012 | Quadri et al. | |
| 2012/0265296 A1* | 10/2012 | McNamara | A61B 17/11 604/503 |
| 2012/0316642 A1 | 12/2012 | Yu et al. | |
| 2012/0323316 A1 | 12/2012 | Chau et al. | |
| 2014/0012368 A1* | 1/2014 | Sugimoto | A61B 17/0057 623/2.11 |
| 2014/0018906 A1 | 1/2014 | Rafiee | |
| 2014/0039083 A1 | 2/2014 | Rafiee | |
| 2014/0128965 A1 | 5/2014 | Rafiee | |
| 2014/0163668 A1 | 6/2014 | Rafiee | |
| 2014/0358223 A1 | 12/2014 | Rafiee et al. | |
| 2015/0025623 A1* | 1/2015 | Granada | A61F 2/2412 623/2.11 |
| 2015/0039084 A1* | 2/2015 | Levi | A61F 2/2409 623/2.38 |
| 2015/0066077 A1* | 3/2015 | Akpinar | A61B 17/0057 606/213 |
| 2015/0134051 A1 | 5/2015 | Donadio et al. | |
| 2015/0134074 A1* | 5/2015 | Walsh | A61F 2/90 623/23.7 |
| 2015/0142094 A1* | 5/2015 | Kassab | A61F 2/86 623/1.11 |
| 2015/0209139 A1* | 7/2015 | Granada | A61F 2/2418 623/2.17 |
| 2016/0375186 A1* | 12/2016 | Tuseth | A61M 60/165 600/16 |
| 2017/0071722 A1* | 3/2017 | Rafiee | A61B 17/11 |
| 2018/0036120 A1* | 2/2018 | Shin | A61F 2/2412 |
| 2019/0231510 A1* | 8/2019 | Rafiee | A61F 2/07 |
| 2019/0321043 A1 | 10/2019 | Rafiee et al. | |
| 2020/0085600 A1* | 3/2020 | Schwartz | A61M 60/152 |
| 2022/0296865 A1* | 9/2022 | Rafiee | A61F 2/88 |
| 2022/0323196 A1* | 10/2022 | Rafiee | A61F 2/064 |
| 2024/0325175 A1* | 10/2024 | McNamara | A61F 2/90 |

FOREIGN PATENT DOCUMENTS

| | | | | |
|---|---|---|---|---|
| EP | 2604223 A1 | 6/2013 | | |
| JP | 2015519969 A | 7/2015 | | |
| KR | 20130110413 A1 | 10/2013 | | |
| KR | 101501614 B1 * | 3/2015 | | A61F 2/82 |
| RU | 100 718 U1 | 12/2010 | | |
| WO | WO-9727898 A1 * | 8/1997 | | A61B 1/3137 |
| WO | 2006121855 A3 | 11/2006 | | |
| WO | WO2007121314 A2 | 10/2007 | | |
| WO | WO2012061809 A2 | 5/2012 | | |
| WO | WO2013131069 A1 | 9/2013 | | |
| WO | WO2015069947 A1 | 5/2015 | | |
| WO | WO2015148821 A1 | 10/2015 | | |

OTHER PUBLICATIONS

International Preliminary Report on Patentability and Written Opinion, or related application No. PCT/US2011/059586, mailed May 25, 2012.

BioIntegral Surgical, Mitral Valve Restoration System.

International Search Report for co-pending international application No. PCT/US2013/028774, mailed Jun. 14, 2013.

International Preliminary Report on Patentability and Written Opinion, on related application No. PCT/US2014/064431 mailed Mar. 26, 2015.

International Search Report, for related application No. PCT/US2015/022782, mailed Jun. 18, 2015.

International Search Report and Written Opinion in Application No. PCT/US2016/052005, mailed Dec. 29, 2016.

International Search Report and Written Opinion in Application No. PCT/US2018/049373, mailed Dec. 6, 2018.

Office Action in related Japanese Patent Application No. JP2018_514884 dated Jun. 30, 2020, with translation.

Extended European Search Report mailed May 24, 2019, from corresponding European Patent Application EP16847336.

(56) References Cited

OTHER PUBLICATIONS

International Search Report dated Jun. 16, 2022 in International Patent Application No. PCT/US2022/018806.
Written Opinion of the International Searching Authority dated May 17, 2022 in International Patent Application No. PCT/US2022/018806.

* cited by examiner

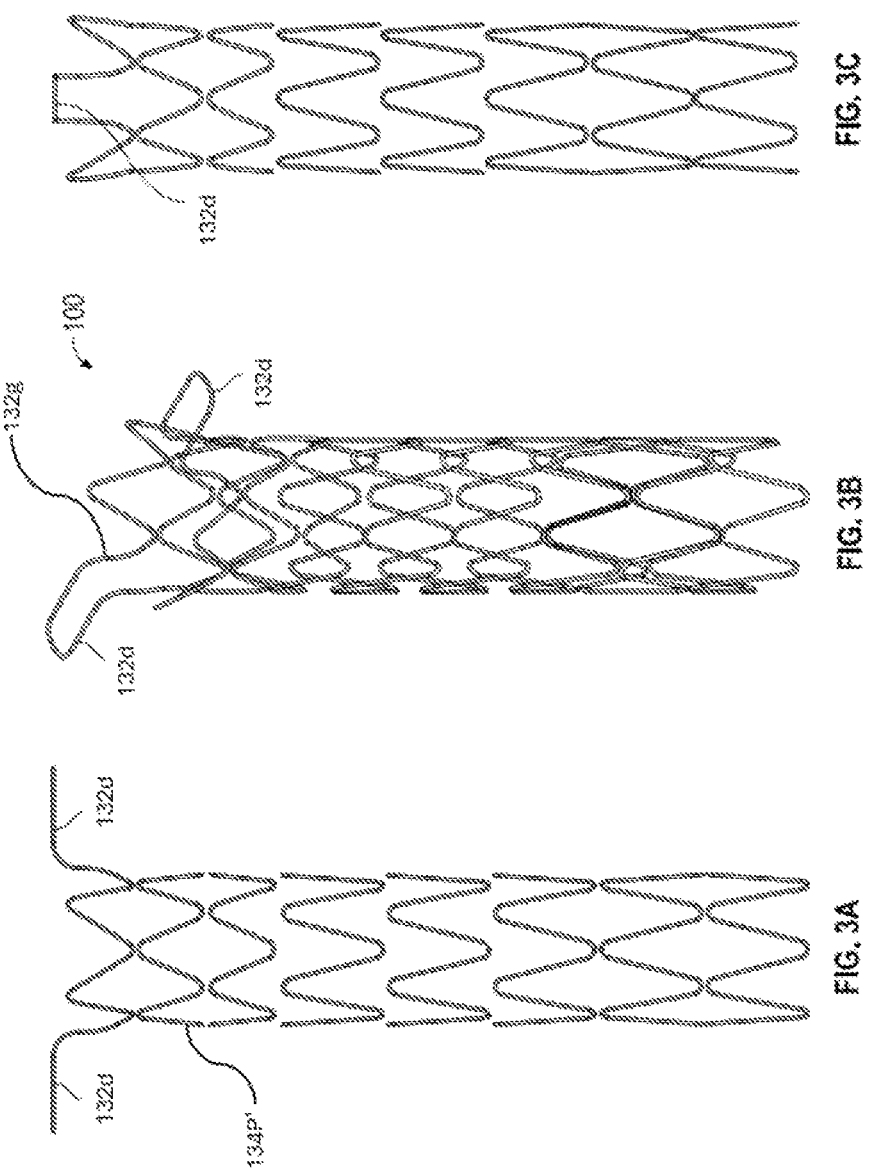

PERCUTANEOUS SHUNT DEVICES AND RELATED METHODS

CROSS-REFERENCE TO RELATED APPLICATIONS

The present patent application is a continuation of and claims the benefit of priority to International Application No. PCT/US18/49373, filed Sep. 4, 2018, which in turn claims the benefit of priority to U.S. Provisional Patent Application Ser. No. 62/553,532, filed Sep. 1, 2017, U.S. Provisional Patent Application Ser. No. 62/615,330, filed Jan. 9, 2018, U.S. Provisional Patent Application Ser. No. 62/615,433, filed Jan. 9, 2018, and U.S. Provisional Patent Application Ser. No. 62/664,722, filed Apr. 30, 2018. The present patent application is also related to U.S. patent application Ser. No. 15/267,075, filed Sep. 15, 2016. Each of the foregoing patent applications is incorporated by reference herein for any purpose whatsoever.

FIELD OF THE DISCLOSURE

The present disclosure relates to devices and methods for transcatheter (i.e., performed through the lumen of a catheter) Glenn shunt and Fontan systems (transcatheter cavopulmonary bypass endograft prosthesis and delivery) for nonsurgical, percutaneous extra-anatomic bypass between two adjacent vessels.

BACKGROUND

Children born with single ventricle physiology (SVP), a form of cyanotic congenital heart disease (CCHD), represent 7.7% of all congenital heart disease patients and have a birth incidence of approximately 4-8 per 10,000. In the United States, this represents approximately 2,000 children born each year. Currently, SVP infants undergo a series of staged surgical procedures. The first palliative procedure establishes a balance between systemic and pulmonary output while minimizing the overload on the single ventricle. The following palliative procedure is often cavopulmonary anastomosis through a bidirectional Glenn shunt or hemi-Fontan procedure to allow for passive pulmonary bloodflow. These are surgical procedures that are invasive and traumatic, requiring significant recuperation time and excessive burden on such a young patient.

SUMMARY OF THE DISCLOSURE

The purpose and advantages of the present disclosure will be set forth in and become apparent from the description that follows. Additional advantages of the disclosed embodiments will be realized and attained by the methods and systems particularly pointed out in the written description hereof, as well as from the appended drawings.

A transcatheter approach for obtaining the results of the surgical procedures described above can revolutionize the management of these children with congenital heart disease. As an alternative to the Norwood Procedure, Bi-directional Glenn operation and Fontan procedure, a nonsurgical transcatheter intervention can limit the burden of surgery for infants while also reducing cost. There is a considerable unmet need for a purpose-built cavopulmonary anastomosis device. To Applicant's knowledge no commercial alternatives exist for off-label medical use.

To achieve these and other advantages and in accordance with the purpose of the disclosure, as embodied herein, in one aspect, the disclosure includes embodiments of a percutaneously deliverable tubular prosthesis to permit an interventional cardiologist to create a shunt between the Superior Vena Cava (SVC) and the main pulmonary artery (MPA). The implant can provide an urgently needed option for children with congenital heart failure to avoid the burden of a three-stage surgery (so called palliative surgery), the burden of an additional heart transplantation after failure of the palliative surgeries, or of the lifelong medication intake after direct heart transplantation.

In some implementations, a tubular prosthesis is provided that includes an elongate compliant tubular body having a proximal end and a distal end, a distal sealing flange coupled to the distal end of the elongate compliant tubular body, the distal sealing flange being configured and arranged to facilitate seating the tubular prosthesis against a first concave vessel wall of a first vessel, wherein the tubular prosthesis is configured to extend outwardly through an ostium formed in the first concave vessel wall when deployed. The distal sealing flange remains inside the ostium after deployment. The tubular prosthesis further includes at least one laterally extending projection that is structurally distinct from the distal sealing flange. The at least one laterally extending projection is located proximate the distal sealing flange, and extends laterally beyond the distal sealing flange. The at least one laterally extending projection is configured and arranged to resist being pulled through said ostium.

Preferably, the at least one laterally extending projection includes two laterally extending projections that are oriented about 180 degrees with respect to each other about a longitudinal axis of the tubular prosthesis. The two laterally extending projections are preferably configured and arranged to rest near a bottom of the first concave vessel wall next to the ostium. Both laterally extending projections are configured and arranged to prevent the distal end of prosthesis from being pulled proximally through the ostium. The two laterally extending projections can be connected to a framework of the tubular prosthesis disposed proximally with respect to the distal sealing flange. For example, the two laterally extending projections can be integrated into a circumferential ring structure that forms a distal end portion of the prosthesis. The circumferential ring structure typically includes an undulating wire that circumferentially traverses a circumference of the tubular prosthesis. The undulating can be defined by a serpentine pattern along at least a part of its length that can have various shapes, such as a sinusoidal shape, a sawtooth shape, a curved wave shape, and the like. One or both of the laterally extending projections can be formed from the same undulating wire that forms the circumferential ring structure.

In some implementations, the circumferential ring structure is formed from an undulating wire that transitions from a serpentine pattern along a first circumferential face of the tubular prosthesis into a first of the two laterally extending projections, transitions from the first of the two laterally extending projections back into the serpentine pattern along a second circumferential face of the tubular prosthesis opposite to the first lateral side of the tubular prosthesis, transitions from the serpentine pattern into the second of the two laterally extending projections along the second circumferential face of the tubular prosthesis, and transitions from the second of the two laterally extending projections back to the serpentine pattern along the first circumferential face of the tubular prosthesis.

In some implementations of the tubular prosthesis, the membrane can be configured to covers the inside and/or outside of the elongate compliant tubular body and the distal flange. For example, the membrane can include a woven or non-woven fabric. If desired, the membrane can include an expanded polytetrafluoroethylene ("ePTFE") material, and/or biological tissue material. If desired, the laterally extending projection(s) may, or may not be covered by the membrane. In some embodiments, the laterally extending projection(s) includes at least one radiopaque marker formed thereon. For example, each of the two diametrically opposed laterally extending projections can include at least one radiopaque marker formed thereon at a location that resides at the ostium during implantation near the base of each of the laterally extending projections. If desired, one or both of the two laterally extending projections further includes at least one radiopaque marker formed near an outward lateral tip of each of the two laterally extending projections, respectively. In some embodiments, the laterally extending projection(s) extend from a location proximal to the distal sealing flange to a location that is distal with respect to the distal sealing flange.

In some implementations of the tubular prosthesis, the distal sealing flange can be formed at least in part from an undulating, star-shaped circumferential wire frame that is structurally distinct from and located distally at least in part with respect to the circumferential ring structure. The undulating, star-shaped circumferential wire frame of the distal flange can be coupled to the circumferential ring structure. The undulating, star-shaped circumferential wire frame of the distal flange can be coupled to the circumferential ring structure by a plurality of fabric filaments, wherein the star-shaped circumferential wire frame of the distal flange is able to move with respect to the circumferential ring structure. If desired, the undulating, star-shaped circumferential wire frame of the distal flange can be coupled to the membrane (such as by stitching and/or adhesive or weaving), and further wherein the circumferential ring structure can be coupled to the membrane. The star-shaped circumferential wire frame of the distal flange can be configured to move or flex with respect to the circumferential ring structure.

In some embodiments, the elongate compliant tubular body can be formed from a plurality of longitudinally spaced undulating circumferential wire frames that are attached to a tubular membrane material. If desired, successive undulating circumferential wire frames (or strut rings) are circumferentially aligned so that they can nest along an axial direction to facilitate bending and shortening (axial collapse) of the prosthesis.

In some embodiments, the tubular prosthesis can further include a proximal sealing flange coupled to the proximal end of the elongate compliant tubular body. The proximal sealing flange is configured and arranged to facilitate seating of the tubular prosthesis against a second concave vessel wall, wherein the tubular prosthesis is configured to extend outwardly through a second ostium formed in the second concave vessel wall when deployed. The proximal sealing flange is configured to remain inside the vessel by the second ostium after deployment. The prosthesis can further include at least one (preferably two diametrically opposed) further laterally extending projection(s) that are structurally distinct from the proximal sealing flange. The at least one further laterally extending projection can be located proximate the proximal sealing flange and extend laterally beyond the proximal sealing flange. The at least one further laterally extending projection is preferably configured and arranged to resist being pulled through said second ostium, wherein upon deployment, the tubular prosthesis forms a closed channel, or shunt, connecting the first concave vessel wall and the second concave vessel wall. Thus, the at least one further laterally extending projection can include two further laterally extending projections oriented about 180 degrees with respect to each other about a longitudinal axis of the tubular prosthesis. The two further laterally extending projections are preferably configured and arranged to rest near a bottom of the second concave vessel wall next to the second ostium, and both further laterally extending projections are preferably configured and arranged to prevent the proximal end of the prosthesis from being pulled distally through the second ostium.

In some implementations, the tubular prosthesis is configured and arranged to self-expand radially outwardly when not constrained. In some embodiments, the tubular prosthesis is configured and arranged to be expanded by an inflatable member of a delivery catheter, for example. In some embodiments, the proximal end of the elongate compliant tubular body can be outwardly flared or bell-shaped to enhance apposition against an interior wall of a second vessel. If desired the tubular prosthesis can define at least one fenestration through a sidewall thereof to permit leakage of bodily fluid through the fenestration.

In some embodiments, the prosthesis can include a membrane that in turn includes an inner layer and an outer layer that cover the inner and outer surfaces of a framework of the prosthesis. In some implementations, the prosthesis can further include at least one elastic body that causes the tubular prosthesis to shorten in length when unconstrained. The at least one elastic body can include at least one tension coil spring that defines a lumen along its length. A central longitudinal axis of the at least one tension coil spring is preferably co-incident (or at least concentric) with a longitudinal axis of the prosthesis. Thus, the tubular prosthesis can be of adjustable telescoping length. Preferably, the inside diameter of the prosthesis remains substantially unchanged when the prosthesis is adjusted in length. The at least one tension coil spring can actually include a plurality of tension coil springs that may be adjacent to or concentrically located with respect to one another.

The disclosure further provides a delivery system including a prosthesis as described elsewhere herein mounted thereon, wherein the prosthesis is mounted on a longitudinal inner member and inside of a retractable sheath. The delivery system can further include at least one removable tether having a first end and a second end. The first and second ends of the tether can be routed through a portion of the prosthesis and extend proximally through and out of a proximal region of the delivery system. The delivery system can further include a first set of radiopaque markers near the distal end of the delivery system, and a second set of markers that are visible outside the patient during a procedure that indicates the relative position of the delivery system and prosthesis. The first and second set of markers can be configured to be maintained in registration with each other during the procedure. For example, the first set of markers can be located on a distal atraumatic tip of the delivery system made of iron oxide to facilitate navigation under MRI or other imaging modality to position the delivery system accurately, and wherein the second set of markers can indicate the relative longitudinal position of the portions of the delivery system. If desired, the markers can be configured to indicate when the distal sealing flange of the prosthesis is suitably configured to pull against an inner face of the wall of a lumen.

The disclosure further provides a delivery system that includes an elongate inner core member having a proximal end and a distal end, the distal end having a compliant atraumatic tip mounted thereon, an inflatable member mounted on the elongate inner core member, a prosthesis as described elsewhere herein mounted around the elongate inner core member, and a retractable sheath having a proximal end and a distal end. The retractable sheath is slidably disposed with respect to, and depending on its position along the elongate core member, selectively covers, the prosthesis and at least a part of the inflatable member. The delivery system can further include a first actuator configured and arranged to advance the sheath proximally with respect to the elongate inner core, inflatable member, and prosthesis, and, a second actuator coupled to a reservoir of fluid. The reservoir is fluidly coupled to the inflatable member, and actuating the second actuator causes the fluid to flow out of the reservoir into the inflatable member to cause the inflatable member to expand radially outwardly.

In some embodiments, the prosthesis is mounted at least partially over and surrounding the inflatable member. For example, a distal portion of the prosthesis can be mounted over the inflatable member, a proximal portion of the prosthesis can be mounted over the inflatable member, or a central portion of the prosthesis can be mounted over the inflatable member. If desired, the prosthesis can be mounted on the elongate inner core member proximally, or distally, with respect to the inflatable member.

In some embodiments, the compliant atraumatic tip can include a gradually tapering distal section that transitions from a larger proximal diameter to a smaller distal diameter. The compliant atraumatic tip can further include a gradually tapering proximal section that transitions from a smaller proximal diameter to a larger distal diameter. A distal end of the proximal section of the compliant atraumatic tip can abut a proximal end of the distal section of the compliant atraumatic tip.

The disclosure further provides methods of delivering and implanting a tubular prosthesis. The method includes providing a delivery system as described herein, delivering a distal end of the delivery system to a target location through the ostium of the first concave vessel wall, withdrawing the sheath proximally to expose the prosthesis, positioning the distal end of the prosthesis in the ostium so that the sealing flange and the at least one laterally extending projection are inside the first concave vessel wall and the elongate compliant tubular body extends through the ostium outside of the first vessel, actuating the second actuator to cause the inflatable member to expand, and expanding the distal end of the tubular prosthesis using the balloon to fit it into the ostium and to shape the sealing flange to fit against the first concave vessel wall.

If desired the inflatable member can be positioned distally with respect to the prosthesis, and the inflatable member can be inflated to outwardly flare the distal end of the prosthesis, as desired. The method can further include adjusting the length of the prosthesis to a desired length. The method can further include disposing a proximal end of the prosthesis inside of a second vessel. For example, the proximal end of the prosthesis can be positioned coaxially inside of an end of the second vessel. Alternatively, the proximal end of the prosthesis can be mounted transversely through a second ostium formed in a wall of the second vessel to shunt the first vessel to the second vessel.

It is to be understood that both the foregoing general description and the following detailed description are exemplary and are intended to provide further explanation of the embodiments disclosed herein.

The accompanying drawings, which are incorporated in and constitute part of this specification, are included to illustrate and provide a further understanding of the method and system of the disclosure. Together with the description, the drawings serve to explain the principles of the disclosed embodiments.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIG. 3A-3C are a lateral side view, an isometric view, and a second lateral side view of a prosthesis in accordance with the present disclosure.

DETAILED DESCRIPTION

Figure 1A:
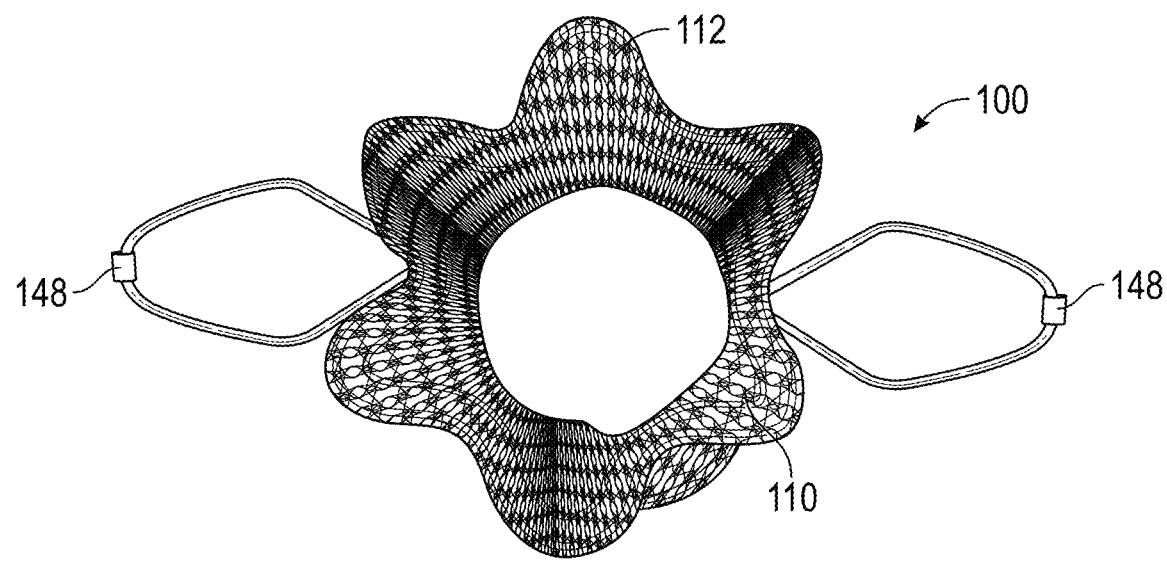
FIGS. 1A-1D depict views for a first embodiment of a prosthesis in accordance with the present disclosure.
Figure 1B:
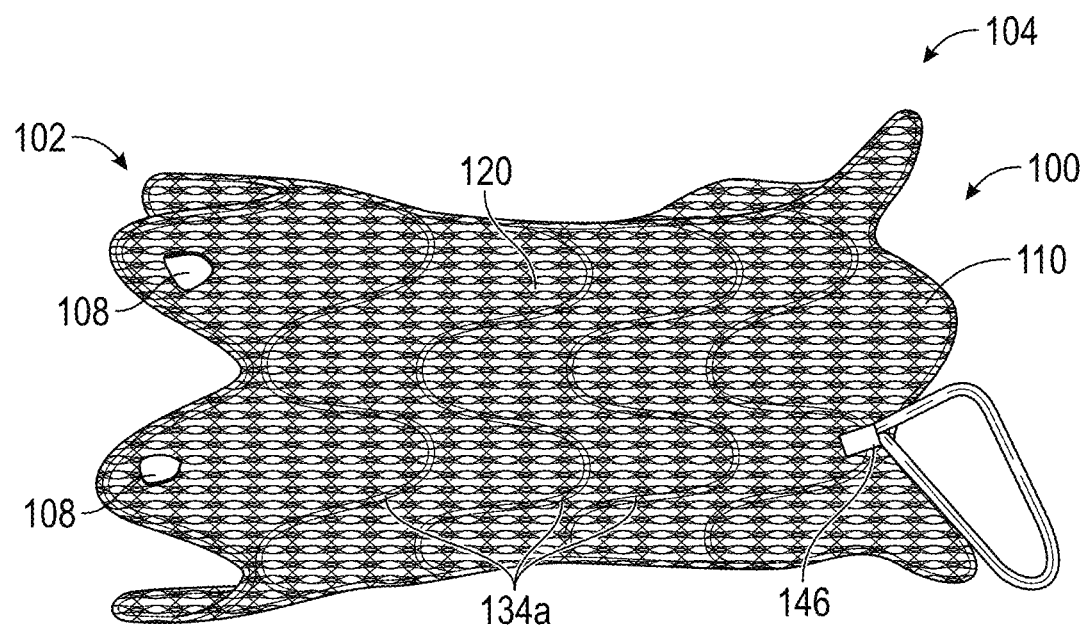
Figure 1C:
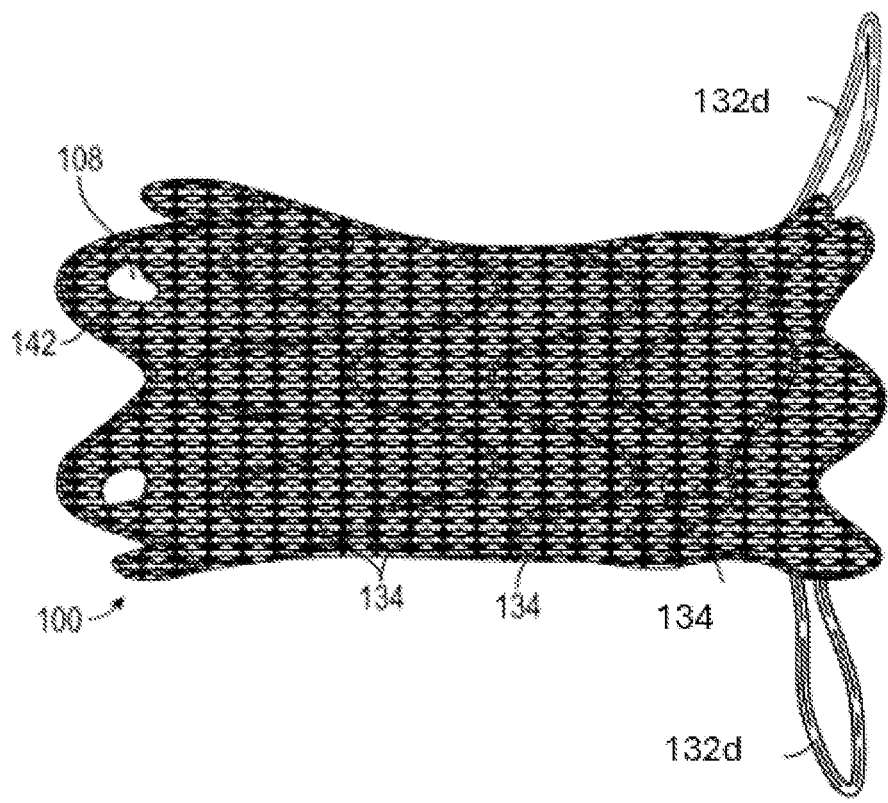

Reference will now be made in detail to the present preferred embodiments of the disclosure, examples of which are illustrated in the accompanying drawings. The methods and corresponding steps of the disclosed embodiments will be described in conjunction with the detailed description of the systems. The exemplary embodiments illustrated herein can be used to perform Glenn, Fontan, and Pott shunting procedures as well as other types of shunting procedures, but in a percutaneous manner. It will be appreciated, however, that the disclosed embodiments, or variations thereof, can be used for a multitude of procedures involving the connection of blood vessels or other biological lumens to native or artificial structures. Such endograft devices represent a potential breakthrough for physicians and young patients who require a safe, less-burdensome, and effective alternative to open heart surgery: a percutaneous approach to heal congenital heart failure.

For purposes of illustration, and not limitation, as embodied herein and as illustrated in FIGS. 1A-1D, a prosthesis 100 is provided that includes an elongate compliant tubular body having a proximal end 102 and a distal end 104. Prosthesis 100 includes a distal sealing flange 110 coupled to the distal end 104 of the elongate compliant tubular body. The distal sealing flange 110 is configured and arranged to facilitate seating the tubular prosthesis 100 against a first concave vessel wall of a first vessel. The tubular prosthesis 100 is configured to extend outwardly through an ostium formed in the first concave vessel wall when deployed. The distal sealing flange 110 remains inside the ostium after deployment. As illustrated, the distal sealing flange 110 is attached to an outer membrane 120, which may be fabric, expanded fluoropolymer (e.g., ePTFE), living tissue (e.g, porcine tissue), and the like. As illustrated, the distal flange is formed by an undulating shaped wire 112 that is in the shape of a six pointed star having six distal vertices 112a and six proximal vertices. The wire 112 is formed into a shape that can lay in a single plane. Preferably, as illustrated, the wire 112 lays in a surface that is conical in shape, or flare-shaped. Thus, when a membrane or fabric is attached to the wire 112, it forms a flared conical surface that is configured and arranged to fit well into an ostium formed in the side wall of a blood vessel, or in the side of a hollow organ (e.g., bladder).

As further illustrated, the tubular prosthesis 100 further includes at least one laterally extending projection 132b that is structurally distinct from the distal sealing flange 110. The at least one laterally extending projection 132b is located proximate the distal sealing flange 110, and, as illustrated, can extend distally beyond the distal sealing flange 110. The at least one laterally extending projection 132b is configured and arranged to resist being pulled through said ostium. In some embodiments, the laterally extending projection(s) extend from a location proximal to the distal sealing flange to a location that is distal with respect to the distal sealing flange.

Preferably, the at least one laterally extending projection includes two laterally extending projections 132b that are oriented about 180 degrees with respect to each other about a longitudinal axis of the tubular prosthesis. The two laterally extending projections 132b are preferably configured and arranged to rest near a bottom of the first concave vessel wall next to the ostium. Both laterally extending projections 132b are configured and arranged to prevent the distal end of prosthesis 100 from being pulled proximally through the ostium. In the illustrated embodiment, the projections 132b are configured to take most of the load for resisting pulling through the ostium, whereas the sealing flange 110, while performing some pull through resistance function, is principally configured to provide a meaningful fluid seal at the intersection of the ostium and the prosthesis 100.

As further illustrated, the two laterally extending projections 132b can be connected to a framework of the tubular prosthesis 100 disposed proximally with respect to the distal sealing flange 110. For example, the two laterally extending projections can be integrated into a circumferential ring structure 132 that forms a distal end portion of the prosthesis, wherein the ring structure is generally located at a location proximal with respect to the sealing flange 110. The circumferential ring structure 132 typically includes an undulating wire that circumferentially traverses a circumference of the tubular prosthesis 100, and defines a cylindrical plane or a conical plane. The undulating wire 132 can be defined by a serpentine pattern along at least a part of its length that can have various shapes, such as a sinusoidal shape, a sawtooth shape, a curved wave shape, and the like having any desired numbers of peaks/valleys 132a. One or both of the laterally extending projections 132b can be formed from the same undulating wire that forms the circumferential ring structure 132.

As illustrated, the circumferential ring structure 132 is formed from an undulating wire that transitions from a serpentine pattern along a first circumferential face of the tubular prosthesis 100 having peaks and valleys 132a into a first of the two laterally extending projections 132a. Projection 132b can have a "U" shape defined by a pair of substantially parallel sections connected by a curved section, or may have a shape that is diamond shaped, as illustrated in FIGS. 1A-1D, for example, wherein the curved tip of each projection 132b angles outward, and then bends back inward at an inflection point, while the wire also follows a path that bends it from a plane that is generally perpendicular to a longitudinal axis of the prosthesis to a plane that is generally parallel to the longitudinal axis of the prosthesis 100.

In some embodiments, the laterally extending projection(s) includes at least one radiopaque marker formed thereon. For example, each of the two diametrically opposed laterally extending projections can include at least one radiopaque marker formed thereon at a location that resides at the ostium during implantation near the base of each of the laterally extending projections. If desired, one or both of the two laterally extending projections further includes at least one radiopaque marker formed near an outward lateral tip of each of the two laterally extending projections, respectively.

For purposes of illustration, as shown in FIG. 1A, the projections 132b include radiopaque marker bands 148 at their outermost tips, as well as marker bands 146 at a proximal location where the ostium can be expected to be located. If desired, the two strands of wire 132 can be crimped together at the location of marker bands 146. During delivery, the individual delivering the prosthesis can endeavor to place marker bands 146 at the location of the ostium while under visualization (e.g., fluoroscopy).

The wire 132 then will typically transition from the first of the two laterally extending projections 132b back into the serpentine pattern along a second circumferential face of the tubular prosthesis opposite to the first lateral side of the tubular prosthesis, and the transition from the serpentine pattern into the second of the two laterally extending projections 132b along the second circumferential face of the tubular prosthesis. The wire then transitions from the second of the two laterally extending projections 132b back to the serpentine pattern along the first circumferential face of the tubular prosthesis.

Figure 1D:
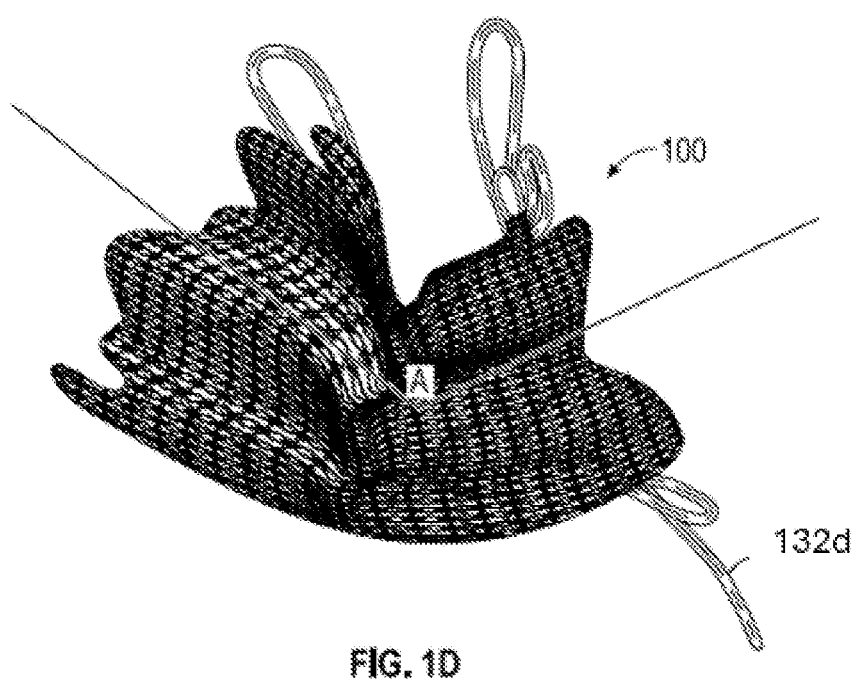
Figure 2A:
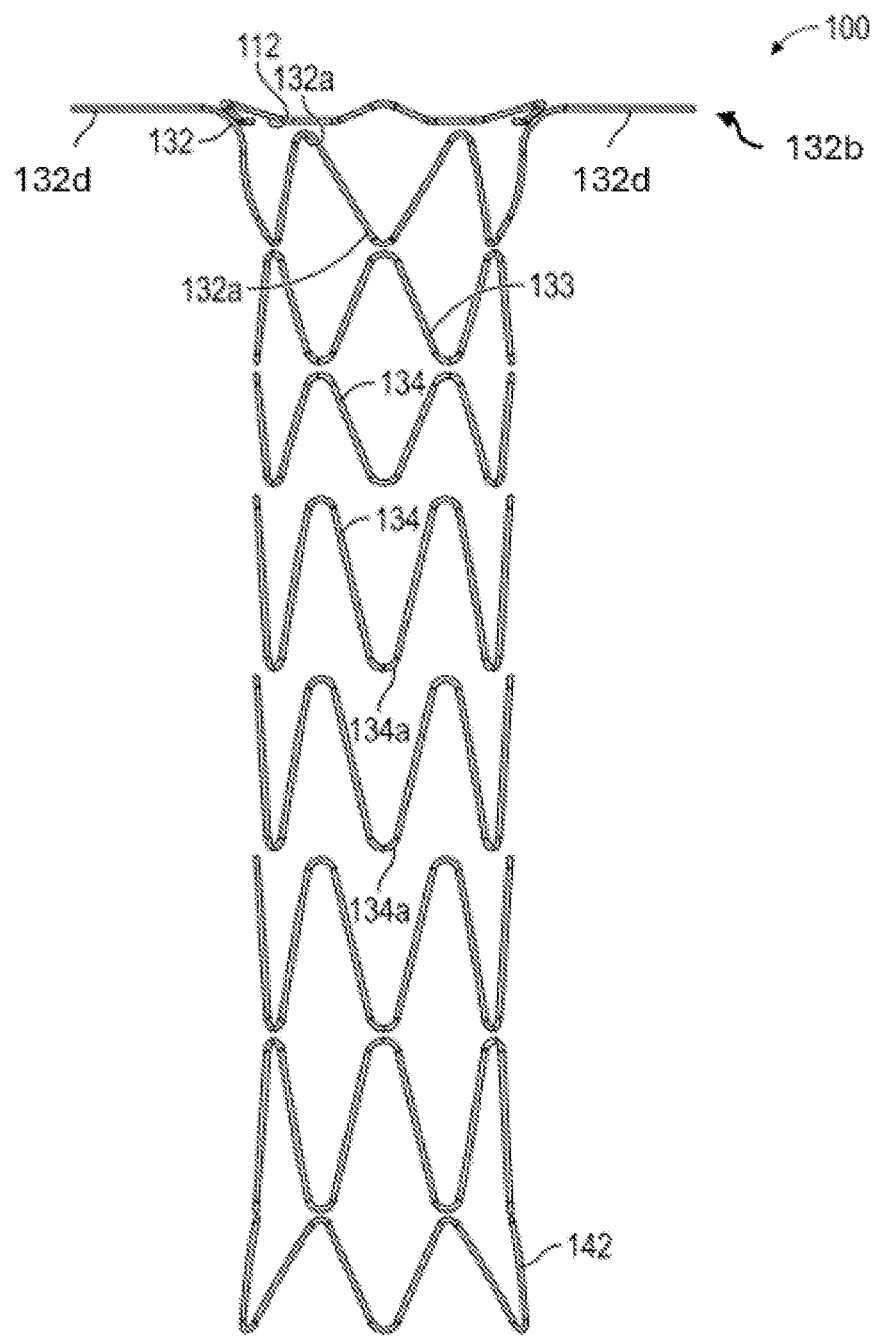
FIGS. 2A-2B are side and top views of a structural frame portion of an embodiment of a prosthesis in accordance with the present disclosure.
Figure 2B:
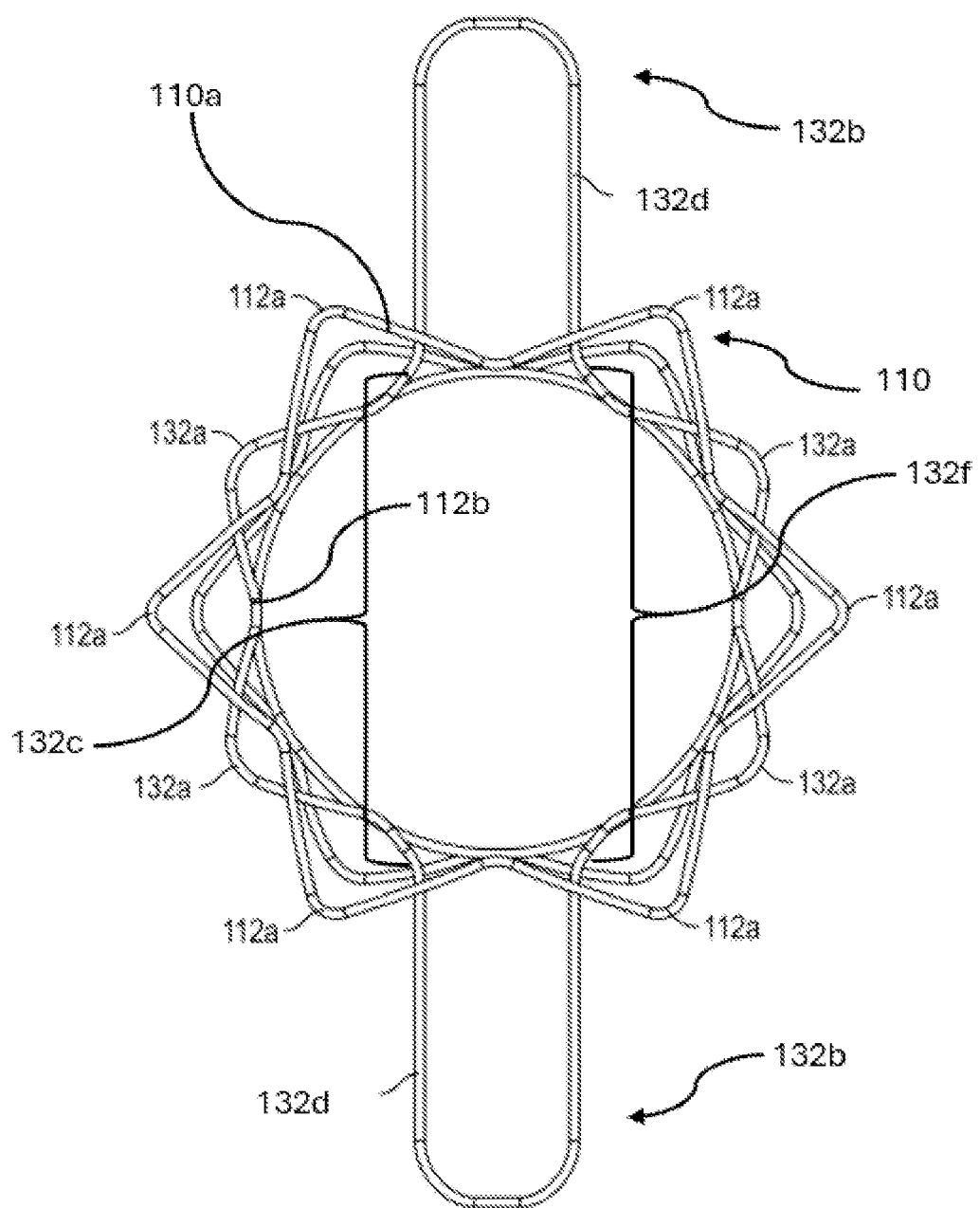

As illustrated in FIGS. 1A and 2A, the framework of the prosthesis further illustrates intermediate sections, rings, or strut rings 134 that have respective peaks and valleys 134a. As can be seen, the rings 134 can be circumferentially aligned such that the peaks and valleys 134a of successive rings 134 are aligned and able to nest, or collapse, into each other along an axial direction. As illustrated in FIG. 1D, the prosthesis is shown being bent by an angle of nearly 120 degrees. The flexibility is a result of the disclosed construction. Moreover, the construction facilitates adjusting the length of prosthesis 100 as well as bending of prosthesis 100 as illustrated in FIG. 1D, wherein the alignment of the peaks 134a in rings 134 permit the rings 134 to collapse into one another. When such axial or bending flexibility is not desired, such as at the interface of rings 133, 134, the apices of the undulations can be aligned. As further illustrated in FIGS. 1A-1D and 2A-2B, a proximal ring 142 can be provided that defines a surface for membrane 120 that is conically flared outwardly. As illustrated, if desired, openings 108 can be defined through the membrane 120 near the apices of the proximal most ring through which a tether can be routed that traverses all or most of the apices, and further wherein both ends of the tether are routed through a delivery system. The tether can be used when deploying the prosthesis 100 to collapse the proximal end of the prosthesis and return it to the delivery system should it be desired to retrieve the prosthesis and remove it from the patient or to reposition it.

In some implementations of the tubular prosthesis 100, the membrane 120 can be configured to cover the inside and/or outside of the elongate compliant tubular body and the distal flange. That is to say, two tubular layers of fabric can be attached to the framework of the prosthesis, both inside the structure of the prosthesis, and outside the framework. The membrane can be sutured, woven, or adhered to the framework of the prosthesis. If inner and outer membranes are provided, they can additionally be attached to each other at various discrete locations along the prosthesis.

The membrane 120 can include a woven or non-woven fabric, for example. If desired, the membrane can include an expanded polytetrafluoroethylene ("ePTFE") material, and/or biological tissue material. If desired, the laterally extending projection(s) 132*b* may, or may not, be covered by the membrane, or may be partially covered. The rings 132, 133, 134, 142, 112 can be attached to the membrane 120, for example, by a plurality of fabric filaments, by stitching, adhesive, weaving, and the like. This permits the star-shaped circumferential wire frame 112 of the distal sealing flange 110 to be configured to move or flex with respect to the circumferential ring structure. Attachment to the fabric of the rings also permits relative flexure of one ring with respect to another due to the presence of the intermediate membrane. If desired, apices of rings can be attached to each other as well in order to provide additional rigidity if needed.

Figure 2C:
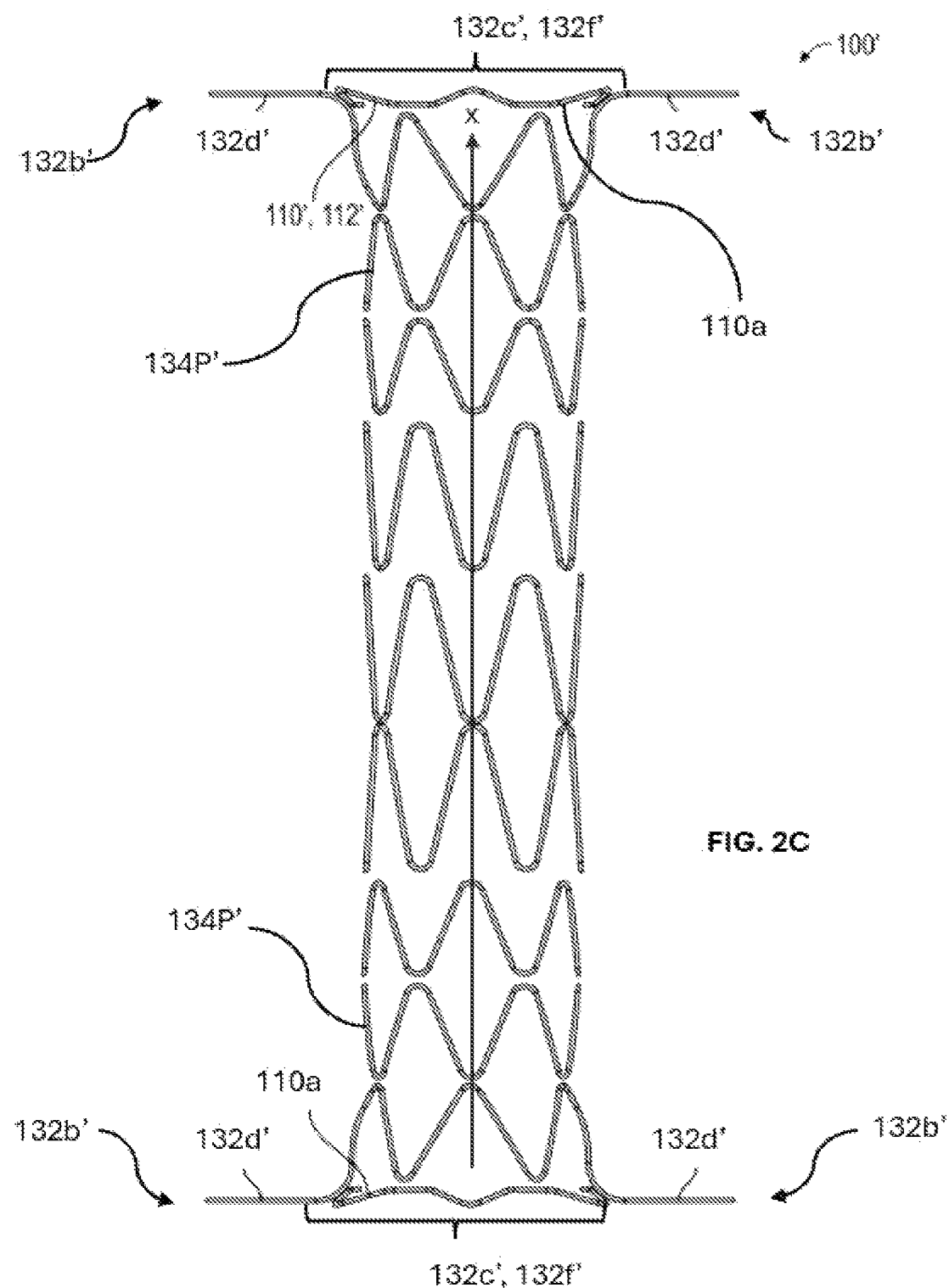
FIG. 2C is a side view of a structural frame portion of a further embodiment of a prosthesis in accordance with the present disclosure.

In some embodiments, a prosthesis can be provided that has the same or similar appearance and structure on the proximal end as well as the distal end. FIG. 2C illustrates an example of a framework for such a prosthesis 100'. Prosthesis 100' can further include both a proximal sealing flange 110' coupled to the proximal end of the elongate compliant tubular body and a distal sealing flange 110' coupled to the distal end of the elongate compliant tubular body. The proximal sealing flange 110' is configured and arranged to facilitate seating of the tubular prosthesis against a second concave vessel wall, wherein the tubular prosthesis 100' is configured to extend outwardly through a second ostium formed in the second concave vessel wall when deployed. The proximal sealing flange 110' is configured to remain inside the vessel by the second ostium after deployment, as with the distal sealing flange. Accordingly, the prosthesis can further include at least one (preferably two diametrically opposed) sets of laterally extending projection(s) 132*b*' that are structurally distinct from the proximal sealing flange. The at least one further laterally extending projection 132' can be located proximate, or near the proximal sealing flange/distal sealing flange 110' and extend laterally beyond the proximal sealing flange 110' as with the embodiment of FIG. 1A. The projections 132*b*' are preferably configured and arranged to resist being pulled through the first and second ostiums of the first and second vessels. Upon deployment, the tubular prosthesis 100' forms a closed channel, or shunt, connecting the first concave vessel wall and the second concave vessel wall. While a membrane covering is not specifically illustrated in FIG. 2C, those of skill in the art will recognize that such a covering is contemplated as for the embodiment of FIG. 1A. Moreover, proximal openings can be provided through the membrane similar to openings 108 of FIG. 1 to permit a tether to be routed through the apices of the proximal flange to help collapse the prosthesis 100' along at least an inward axial direction. Thus, the at least one further laterally extending projection(s) can include two further laterally extending projections 132*b*' oriented about 180 degrees with respect to each other about a longitudinal axis of the tubular prosthesis on both ends of the prosthesis 100'. If desired, prosthesis 100, 100' can additionally be provided with one or more elastic members, such as tension coil springs, or tubular elastic material, that can surround the framework of the prosthesis 100, 100' and cause the prosthesis to shorten along its length. FIGS. 3A-3C illustrate a framework for a version of prosthesis 100 that does not include a sealing flange 110. If desired, this version of the prosthesis can otherwise be identical to embodiment 100 of FIG. 1A but for the presence of the sealing flange. As will be appreciated, the projections 132*b* can be used in order to prevent the prosthesis from being pulled through the ostium. As with the embodiment of FIG. 2C, the embodiment of FIGS. 3A-3C can likewise have projections 132*b* at both the proximal and distal ends of the prosthesis for shunting two vessels, as desired.

As set forth above, and with continuing reference to FIGS. 1C, 1D, 2A-2C and 3A-3C, implementations of a tubular prosthesis (100, 100') are provided that include an elongate compliant tubular body having a proximal end and a distal end. The elongate compliant tubular body is formed at least in part from a plurality of undulating strut rings (134, 134') arranged axially along a central longitudinal axis X (FIG. 3C) of the tubular prosthesis. The central longitudinal axis defines an axial direction. The prosthesis further includes a distal sealing flange (110, 110') that is operably coupled to the distal end of the elongate compliant tubular body. The distal sealing flange is formed at least in part from a first undulating filament (110*a*, 110*a*') that is configured into a shape of a multi-pointed star having a first plurality of convex radially outwardly directed vertices 112*a* separated by a second plurality of radially inwardly directed concave vertices 112*b*. The distal sealing flange 110, 110' is configured and arranged to facilitate seating the tubular prosthesis against a first concave vessel wall of a first vessel, wherein the tubular prosthesis is configured to extend outwardly through an ostium formed in the first concave vessel wall when deployed, wherein the distal sealing flange remains inside the ostium after deployment.

The prosthesis further includes two opposing laterally extending projections 132*b* that are operably coupled to the elongate compliant tubular body. Each opposing laterally extending projections 132*b* is formed by a respective loop portion (132*d*, 132*d*') that in turn is formed from a second filament 132*g* (FIG. 3B) that is shaped into a distal strut ring that is structurally and physically distinct from the distal sealing flange having a first circumferential portion 132*c*, 132*c*' formed by a first set of undulations that lay in a cylindrical plane that surrounds the longitudinal axis and a second circumferential portion 132*f*, 132*f*' formed by a second set of undulations that also lay in the cylindrical plane, wherein the first circumferential portion 132*c*, 132*c*' and the second circumferential portion 132*f*, 132*f*' are joined to each other by the two laterally extending loop sections, wherein the distal strut ring is located along the axial direction between the distal sealing flange and a penultimate undulating strut ring 134P, 134P' of the plurality of undulating strut rings, wherein the two laterally extending loop sections 132*d*, 132*d*' that extend radially outwardly to a width that is wider than a maximum lateral width of the distal sealing flange 110, 110'. The two laterally extending loop sections 132d, 132d' are configured to rest in a bottom of the first concave wall of the first vessel on either side of said ostium beyond an outward radial extent of the distal sealing flange to prevent the prosthesis from being pulled through said ostium after deployment.

Further embodiments of an axially collapsible prosthesis 200, 300, 400 are illustrated in FIGS. 5A-5H. These prostheses are generally similar in that they include an axially collapsible body that is typically defined by a helical spring, such as a tension spring, or similar member.

Figure 5A:
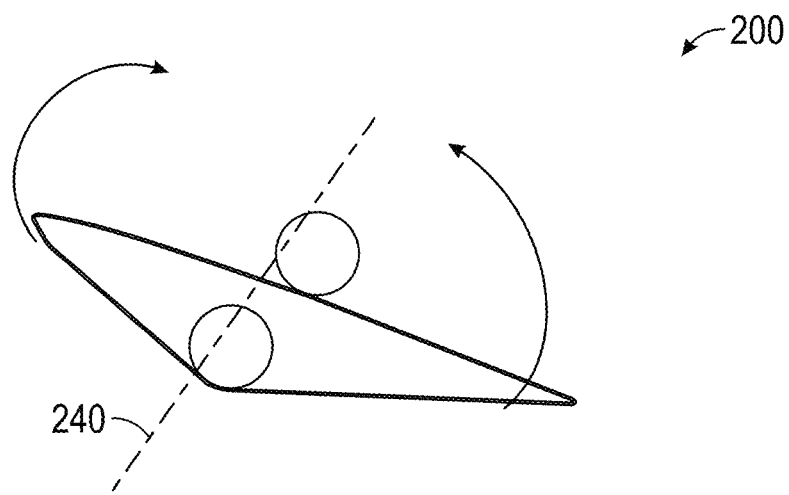
FIGS. 5A-5B are views of a further embodiment of a structural frame portion of an embodiment of a prosthesis in accordance with the present disclosure.
Figure 5B:
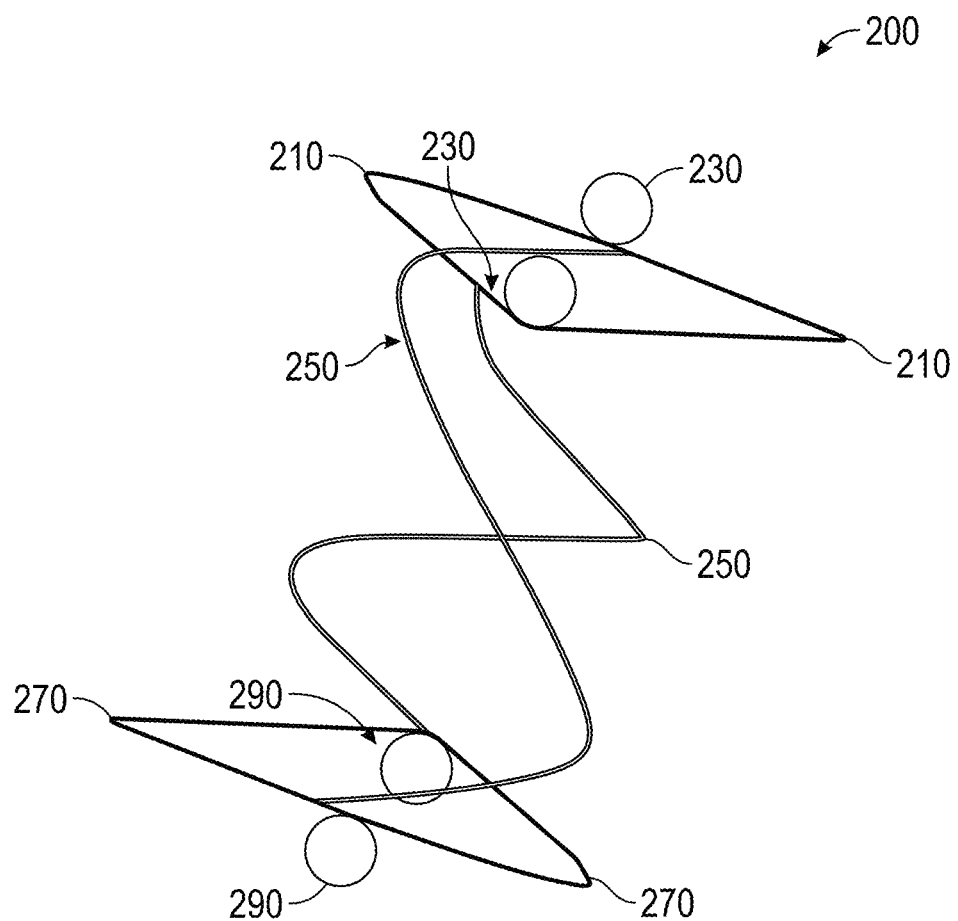

For purposes of illustration, FIGS. 5A-5B are views of a further embodiment of a structural frame portion of an embodiment of a prosthesis in accordance with the present disclosure. The example in FIG. 5A includes a collapsible prosthesis including folding lateral wings and a collapsible coil extending along the length of the prosthesis. As illustrated, each end of the prosthesis 200 includes folding lateral wings, 210 and 270. Folding lateral wings 210 are disposed on a first end of the prosthesis 200, and folding lateral wings 270 are disposed on a second end of the prosthesis opposite the first end, though folding lateral wings 210, and 270 are structurally the same, but physically inverted with respect to each other, and if desired, rotationally aligned with each other about a longitudinal axis of the prosthesis 200. The folding lateral wings 210, 270 are configured to articulate orthogonally about an axis 240 via coils 230, 290. Coils 230 and wings 210/270, as illustrated are wound from the same strand of wire, such as NiTi alloy wire. Wings 210 fold inward towards one another by virtue of tension being wound into coils 230. This distributes the bending stress for the wings over a longer length of material, which can be advantageous as Ni Ti alloys tend to be brittle if bend over too short of a distance. In such a manner, folding lateral wings 210, in the folded state, may be compressed radially inwardly toward a central axis of the prosthesis 200 to facilitate reducing the profile of the prosthesis 200 to permit it to be collapsed and drawn into a delivery sheath of a delivery catheter. Folding lateral wings 270 are similarly configured to fold towards one another via folding, or "winding" coils 290 with tension.

As alluded to above, the folding lateral wings 210, 270, as well as the folding coils 230, can be comprised of a uniform heat formed wire, such as heat set nitinol, among other examples. For example, folding lateral wings 270, as well as folding coils 290 can be comprised of a uniform piece of wire heat shaped to extend laterally from the prosthesis in the uncompressed form, as illustrated in FIGS. 5A-5B. Each of the folding lateral wings 270, 290 may apply a force against a side wall of a vessel within which the prosthesis 200 is deployed, thereby preventing the prosthesis from being removed from an ostium formed through the vessel in a manner similar to wings/protrusions 132a discussed above. The end sections formed by wings 210/270 are also illustrated as being coupled to one or more (e.g, two or three) longitudinal coils 250. As illustrated, the collapsible coils 250 extend along a longitudinal length of the prosthesis, and couple the end sections to each other. As illustrated, each of the two coils 250 are out of phase with each other by about 180 degrees about a longitudinal axis of the prosthesis 200. In this manner, the coils 250 can structurally support inner and/or outer membrane layers to define a lumen through the prosthesis. Preferably, the coils 250 are evenly spaced from each other in this manner, such that two coils, as illustrated are spaced from each other about the axis, or out of phase, so to speak by 180 degrees, three coils are spaced from each other by 120 degrees, and four coils are spaced from each other by 90 degrees, and so on.

Figure 5C:
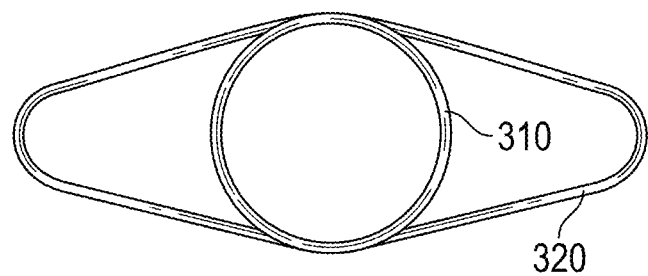
FIGS. 5C-5D are views of still a further embodiment of a structural frame portion of an embodiment of a prosthesis in accordance with the present disclosure.
Figure 5D:
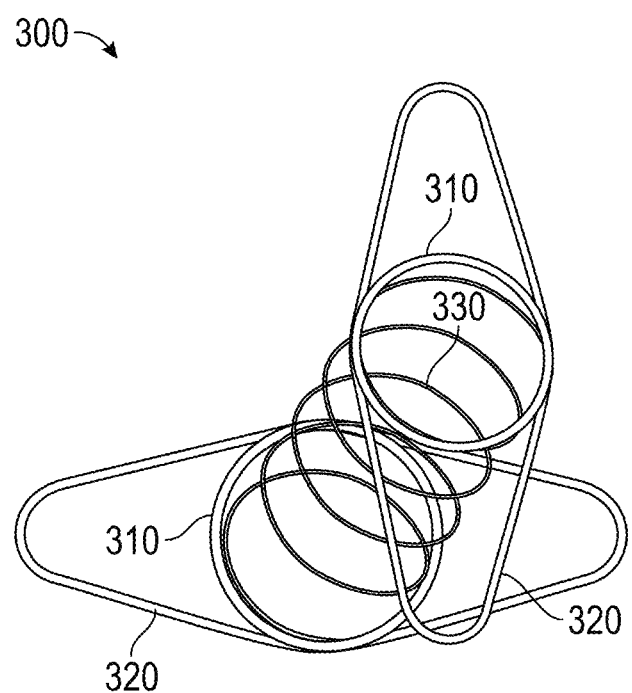

FIGS. 5C and 5D illustrate a further embodiment of a framework for a prosthesis 300. FIG. 5C illustrates structural supports of the end portions of the prosthesis 300. As illustrated, each end portion of prosthesis 300 includes an inner frame 310 coupled to an outer frame 320. Inner frame 310 and outer frame 320 can be made from the same piece of material wound about a mandrel (e.g., NiTi alloy wire) or different pieces of material that are attached to each other, for example, by soldering or welding. While inner frame 310 is circular, it will be appreciated that it may be other shapes, such as oval or polygonal. Outer frame 320, as presented, includes a widened central portion that aligns with the curvature of the inner frame 310 that tapers down on both sides to a projection, or wing, that is similar in function to wings 132b, 210, 270 described above, in that they are configured to prevent prosthesis 300 from being pulled through an ostium formed in a vessel wall. If desired, sealing flanges similar to those of FIG. 1A can be attached, for example to inner frame 310, extending toward the other end of the prosthesis, to provide a tapered sealing surface to fit into the ostium formed in the wall of a vessel or hollow organ.

Figure 5E:
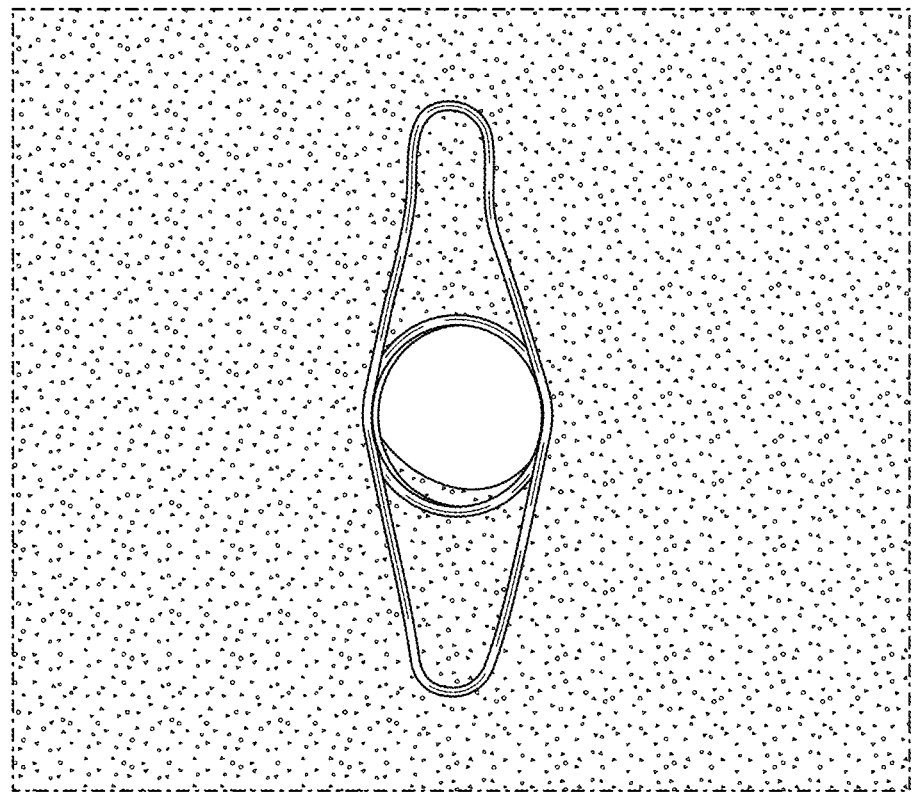
FIGS. 5E-5F are views of the embodiment of a structural frame portion of FIGS. 5C to 5D in situ across a piece of simulated tissue.
Figure 5F:
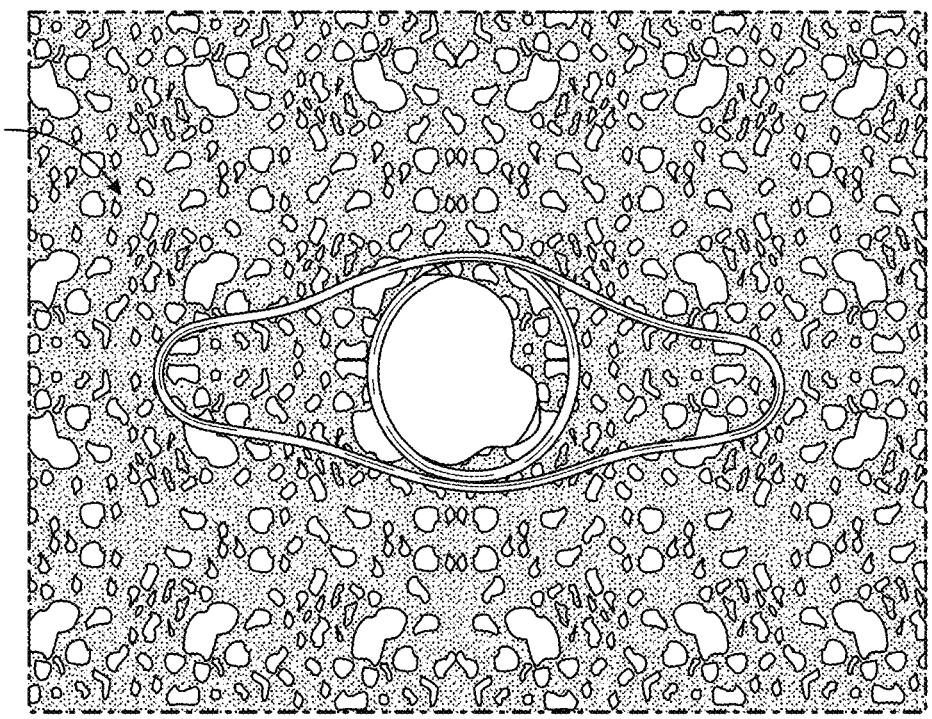

As illustrated in FIG. 5D, the end frame portions, or flanges, of prosthesis 300 can be connected to each other by one or more coil springs in the same manner as prosthesis 200. While only one spring 330 is shown, it will be appreciated that multiple coil springs that can be used that are of different overall diameters such that they can nest inside one another. If desired, the springs 330 can additionally or alternatively be rotationally spaced from each other evenly or unevenly about a central longitudinal axis of the prosthesis 300. If desired, the end flanges of prosthesis 300 can additionally or alternatively be connected by strut rings and membrane material in a manner similar to the embodiment of FIGS. 1A-1D. As illustrated, the end flanges (310, 320) of prosthesis are rotated 90 degrees with respect to one another about a longitudinal axis of the prosthesis 300. As will further be appreciated, regardless as to the structural framework of prosthesis 300, prosthesis 300 preferably includes inner and/or outer membrane, or fabric, layers as with the layer(s) 120 of embodiment 100 as set forth in FIGS. 1A-1D. FIGS. 5E and 5F illustrate the framework of prosthesis 300 deployed in a thick piece of material intended to simulate tissue, such as two nearby blood vessels to be shunted to each other.

Figure 5G:
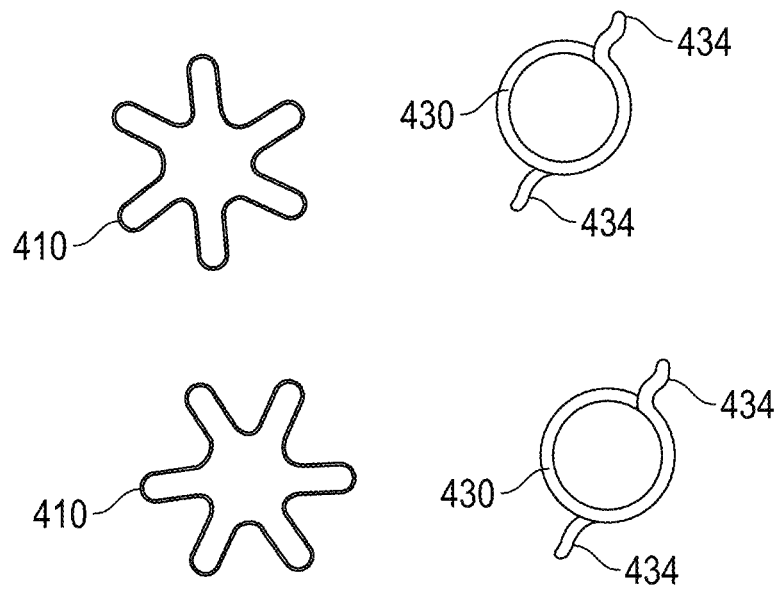
FIGS. 5G and 5H illustrate aspects of still a further embodiment of a prosthesis in accordance with the present disclosure.
Figure 5H:
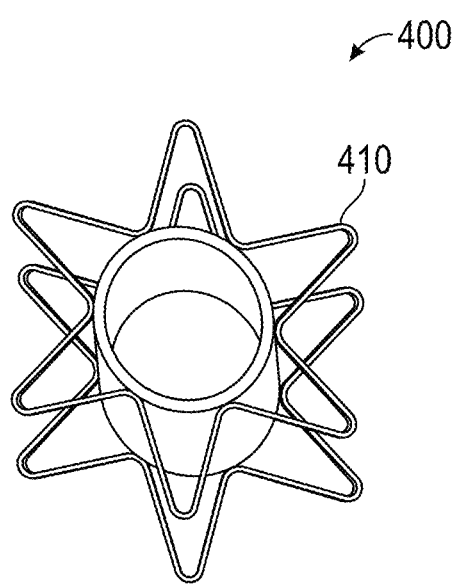
Figure 5I:
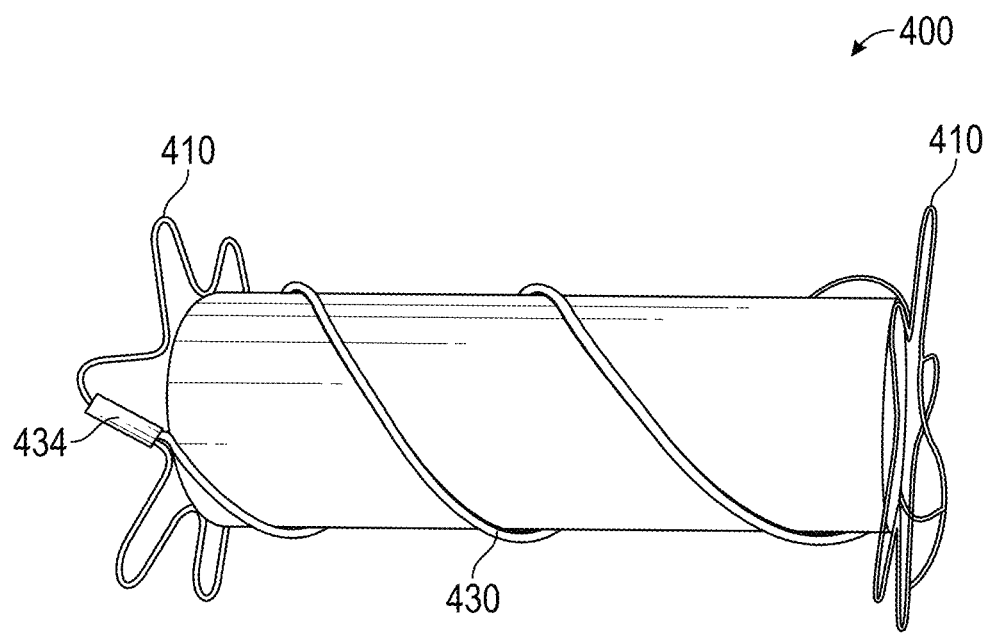
FIG. 5I illustrates the structural frame portion of FIGS. 5G-5H stretched over a cylindrical mandrel.
Figure 5J:
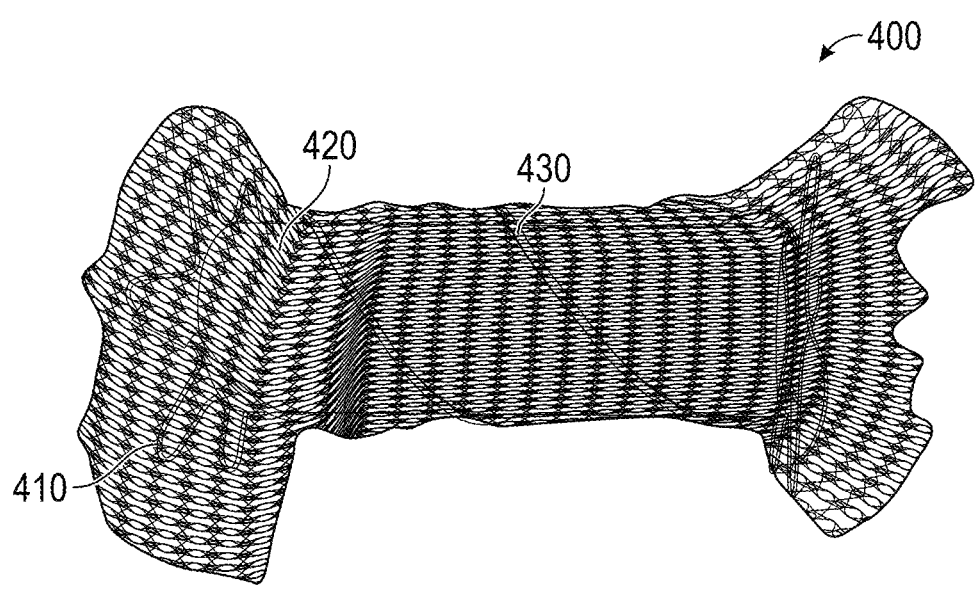
FIG. 5J illustrates the structural frame portion of FIGS. 5G-5H stretched over a cylindrical mandrel and covered with a suitable membrane material.

FIG. 5G illustrates components an embodiment of a prosthesis 400 in accordance with the present disclosure illustrated in various stages of assembly in FIGS. 5H, 5I and 5J. Prosthesis includes a structural frame portion including proximal and distal flanges 410 connected to each other by one or more (e.g., two) tension coil springs 430. In particular, flanges 410 are similar to flange frame 112 of sealing flange 110 of FIG. 1A. Similar to the embodiment of FIG. 1A, prosthesis 400 includes proximal and distal sealing flanges that are preferably at least partially covered in fabric or other membrane 420 (FIG. 5J). The coil springs 430 each include two terminal projections 434 that are attached to radially oriented portions of flanges 410, for example, by way of soldering or welding, to provide a strong joint. Multiple coils that are evenly or unevenly spaced that can nest within each other can be provided as described with respect to prosthesis 300 illustrated hereinabove. FIG. 5H illustrates an end view of prosthesis 400 clearly showing flange 410. If desired, one or more marker bands can be provided on flange 410. Alternatively, flange 410 and/or coil spring(s) 430 can be made from radiopaque material. Membrane material 420 can be provided inside, outside, and/or in between coil springs 430 for prosthesis 400. Also, if desired, strut rings can be substituted for coil springs 430 in prosthesis 400 as with the embodiment of FIG. 1A.

Figure 5K:
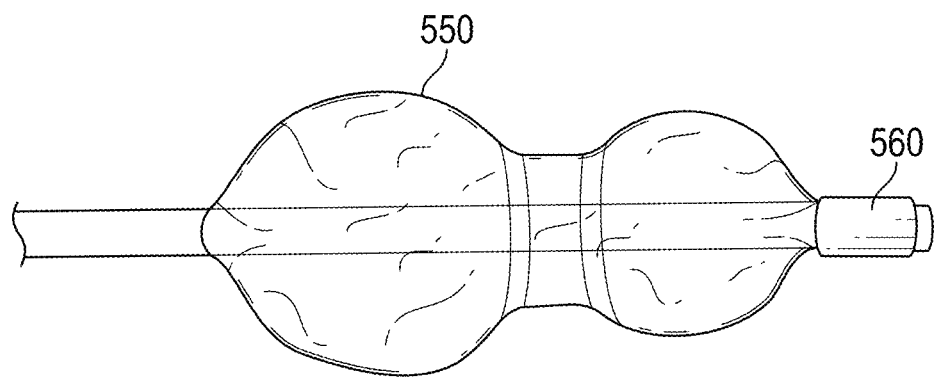
FIGS. 5K-5M illustrates views of a distal end portion of a further delivery system for delivering a prosthesis in accordance with the present disclosure.
Figure 5L:
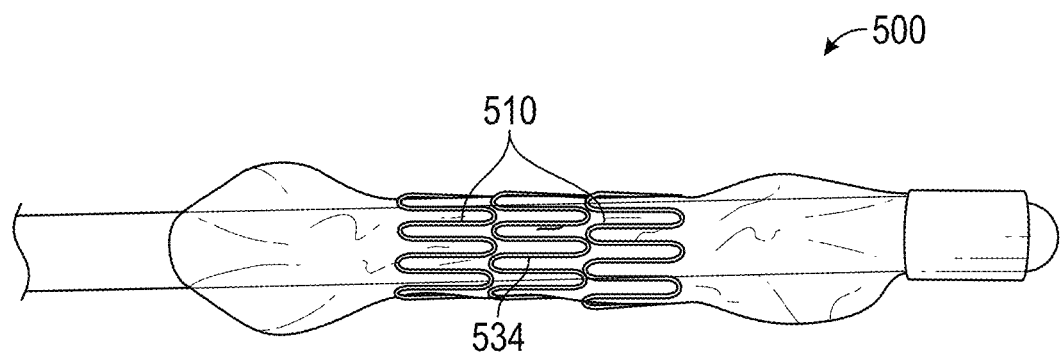
Figure 5M:
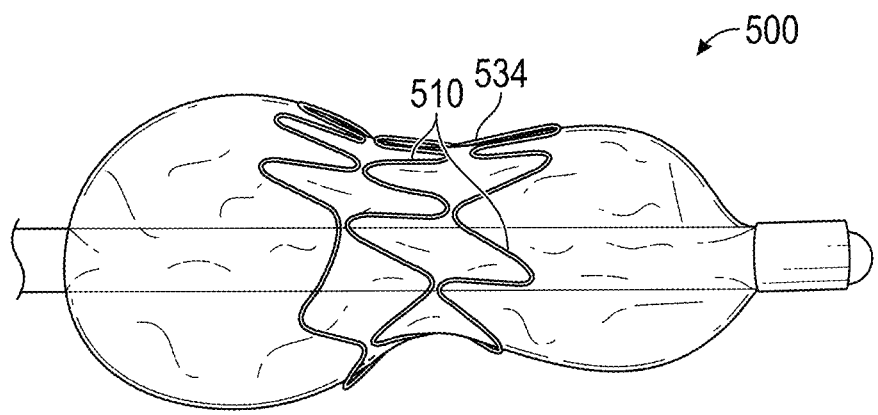

FIGS. 5K-5M illustrate additional embodiments of a collapsible prosthesis 500, in accordance with the present disclosure. FIGS. 5A-5D illustrate a collapsible prosthesis 500 including proximal and distal flanges 510 attached to each other by an undulating strut ring 534, similar to those described with respect to FIG. 1A. Prosthesis can be crimped onto a distally formed balloon 550 that is in turn mounted to an elongate inner member 560 of a delivery system. Prosthesis 500 can be collapsed radially inwardly (e.g., by crimping) onto balloon 550. As illustrated in FIGS. 5K-M, a dual-lobed balloon including a proximal bulb and a distal bulb connected by a neck portion may be used to expand and outwardly flare the flanges 510 of prosthesis 500, for example, to form a shunt between two nearby vessels. The dual-lobed balloon can be formed from separate inflatable balloons, or a singular inflatable enclosure with a narrowed neck as illustrated. Prosthesis 500 is preferably provided with an inner and/or outer membrane covering (not shown). FIG. 5K illustrates the balloon in an inflated condition, FIG. 5L illustrates the prosthesis (illustrating the frame only) 500 crimped on the balloon prior to delivery and FIG. 5M shows the prosthesis 500 in a partially deployed condition by virtue of inflating the balloon. Such a balloon with multiple lobes, or proximal and distal neck regions and a larger central lobe can be used to selectively flare ends of prostheses as described below.

In general, it will be appreciated that any of the prostheses disclosed herein can further include at least one elastic body (e.g., tension coil spring) that causes the tubular prosthesis to shorten in length when unconstrained. The at least one elastic body can include at least one tension coil spring that defines a lumen along its length. A central longitudinal axis of the at least one tension coil spring is preferably co-incident (or at least concentric) with a longitudinal axis of the prosthesis. Thus, the tubular prosthesis can be of adjustable telescoping length. Preferably, the inside diameter of the prosthesis remains substantially unchanged when the prosthesis is adjusted in length. The at least one tension coil spring can actually include a plurality of tension coil springs that may be adjacent to or concentrically located with respect to one another.

The disclosure further provides a delivery system including a prosthesis as described elsewhere herein mounted thereon For purposes of illustration, and not limitation, FIGS. 4A-4H illustrate aspects of a delivery system for delivering a prosthesis as set forth herein above.

Figure 4A:
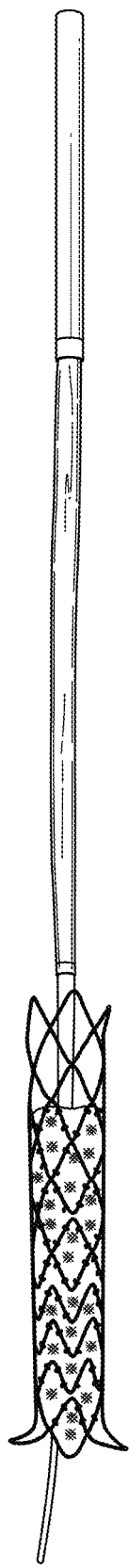
FIG. 4A-4H are various views of a delivery system for a prosthesis in accordance with the present disclosure.
Figure 4B:
Figure 4C:
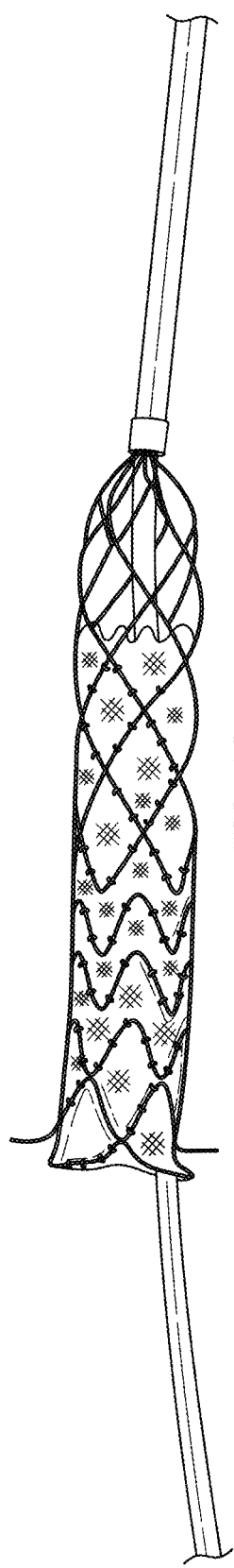
Figure 4D:
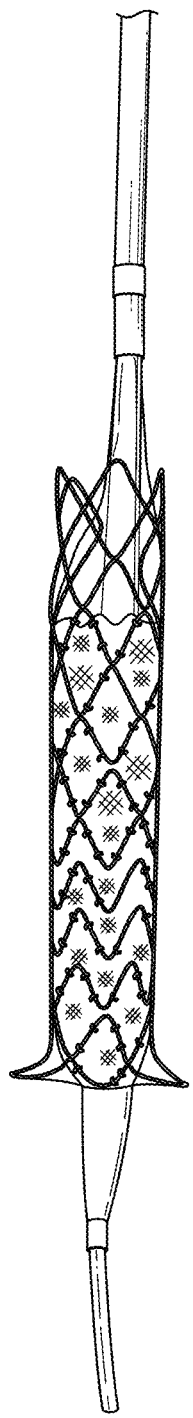
Figure 4E:
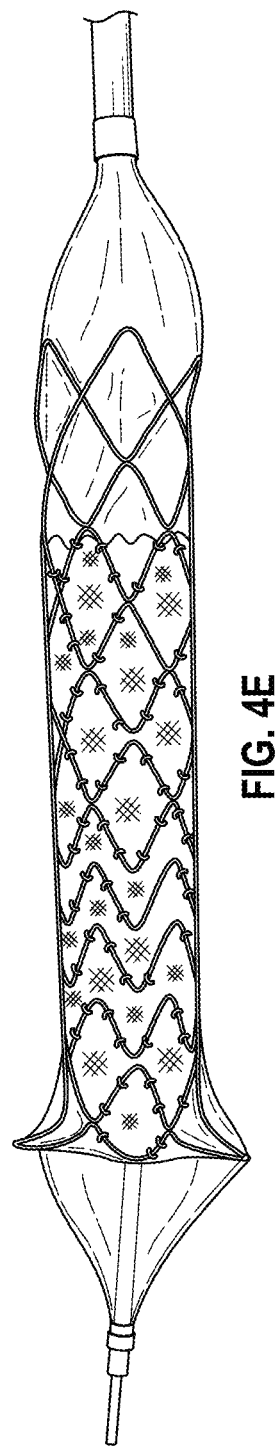
Figure 4F:
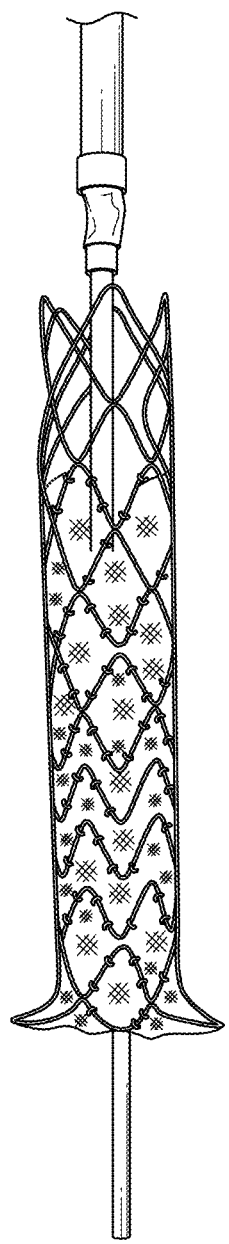
Figure 4G:
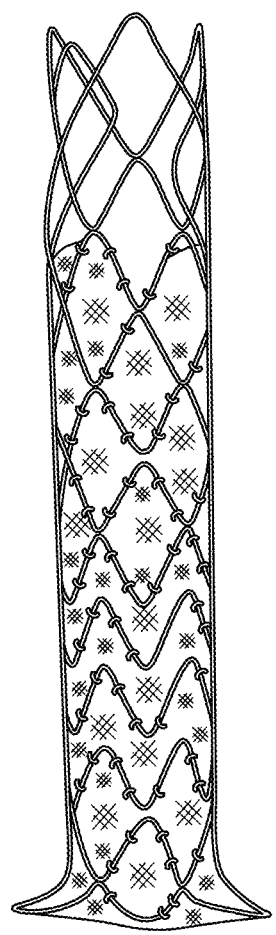
Figure 4H:

As illustrated in FIGS. 4A-4H, a prosthesis similar in construction to that in FIGS. 1A-1D is mounted on a longitudinal inner member of a delivery system. The delivery system includes an elongate inner core member having a proximal end and a distal end. The distal end has a compliant atraumatic tip mounted thereon that may have a gradual distal taper, and may also include a proximal taper as illustrated in FIG. 4H to ease removal of the distal end of the delivery system from a blood vessel back into a shunt that has been mounted as the delivery system is being withdrawn.

As depicted, the delivery system includes an inflatable member mounted on the elongate inner core member, and the prosthesis (e.g., 100) is mounted around the elongate inner core member. A retractable sheath is also provided having a proximal end and a distal end. The retractable sheath is slidably disposed with respect to, and depending on its position along the elongate core member, selectively covers, the prosthesis and at least a part of the inflatable member. The delivery system can further include a first actuator (not shown) configured and arranged to advance the sheath proximally with respect to the elongate inner core, inflatable member, and prosthesis. A second actuator can be coupled to a reservoir of fluid. The reservoir is fluidly coupled to the inflatable member, and actuating the second actuator causes the fluid to flow out of the reservoir into the inflatable member to cause the inflatable member to expand radially outwardly. Specifically, for purposes of illustration, FIG. 4A shows a distal portion of the delivery system showing a deployed prosthesis located distally with respect to a balloon used for inflation, whereas FIG. 4B shows the uninflated, elongate balloon without the prosthesis being present. FIGS. 4C-4G show the balloon in various stages of inflation.

In some embodiments, the prosthesis can be mounted at least partially over and surrounding the inflatable member. For example, a distal portion of the prosthesis can be mounted over the inflatable member, a proximal portion of the prosthesis can be mounted over the inflatable member, or a central portion of the prosthesis can be mounted over the inflatable member. If desired, the prosthesis can be mounted on the elongate inner core member proximally, or distally, with respect to the inflatable member.

An exemplary method in accordance with the disclosure includes providing a delivery system as described herein, delivering a distal end of the delivery system to a target location through the ostium of the first concave vessel wall, withdrawing the sheath proximally to expose the prosthesis, positioning the distal end of the prosthesis in the ostium so that the sealing flange and the at least one laterally extending projection are inside the first concave vessel wall and the elongate compliant tubular body extends through the ostium outside of the first vessel, actuating the second actuator to cause the inflatable member to expand, and expanding the distal end of the tubular prosthesis using the balloon to fit it into the ostium and to shape the sealing flange to fit against the first concave vessel wall.

If desired the inflatable member can be positioned distally with respect to the prosthesis, and the inflatable member can be inflated to outwardly flare the distal end of the prosthesis, as desired. The method can further include adjusting the length of the prosthesis to a desired length. The method can further include disposing a proximal end of the prosthesis inside of a second vessel. For example, the proximal end of the prosthesis can be positioned coaxially inside of an end of the second vessel. Alternatively, the proximal end of the prosthesis can be mounted transversely through a second ostium formed in a wall of the second vessel to shunt the first vessel to the second vessel.

As to further embodiments, of methods, a shunt as set forth herein can be constructed as a "Glenn Shunt" (about 5 cm in length) or a "Fontan Shunt" (about 8 cm in length). These can be, for example, super elastic Nitinol-supported tubular polyester fabric implants that are delivered through a specially designed delivery system. Preferably, the prosthesis and delivery system are both MRI compatible. The illustrated TCBE embodiments can incorporate several useful features specifically developed for transcatheter cavopulmonary bypass. A pediatric shunt can be provided in a variety of sizes, such as between about 15 mm and about 50 mm in length, such as 25 or 30 mm in length, and about 10 mm in diameter.

In a Glenn procedure, a distal flanged end of a prosthesis (e.g., of FIG. 1A) pulls against the inner wall of the main pulmonary artery (MPA), with the proximal end of the prosthesis extending into the superior vena cava. For a Fontan procedure, the prosthesis can include one or more (e.g., 2) fenestrations through the fabric in a central region of the shunt to permit leakage into the right atrium when the prosthesis spans from its distal end situated within the main pulmonary artery to the superior vena cava. Thus, in the Fontan procedure, the shunt can be used to connect the inferior vena cava (IVC) through the right ventricle to the main pulmonary artery (MPA)), wherein the prosthesis includes fenestrations to permit leakage through the prosthesis into the ventricle.

Pulmonary hypertension of diverse etiologies causes severe symptoms and high mortality rate. Symptoms include inability to exercise, shortness of breath, right-sided congestive heart failure, and sudden death. New pharmacologic options have significantly prolonged survival in adults with severe pulmonary hypertension. These therapeutic options have led to nationwide centers of excellence for the care of pulmonary hypertension. Despite successful pharmacotherapy, the disease progresses in the majority causing progressive right ventricular failure and declining functional status. Heart-lung transplantation may not be an option.

Forming a "Potts" shunt (between the left pulmonary artery and the descending thoracic aorta) is a surgical procedure that can divert blood flow to relieve right heart failure in patients with end-stage pulmonary hypertension. It can be offered as a bridge to transplantation or as a destination therapy. Surgical Potts shunt is morbid and complex. In accordance with the present disclosure, a catheter-based Potts shunt (such as that illustrated in FIGS. 5A-5J can be delivered by way of a delivery system as set forth herein and used to shunt the left pulmonary artery to the descending thoracic aorta.

If desired, in some embodiments, the proximal end of the prosthesis (e.g., 100, 100', 200, 300, 400, 500) can receives a tether therethrough that is routed through the windings of the most proximal undulating strut ring through openings defined in membrane material (e.g., 120). The tethers are withdrawn proximally through a tubular member (e.g., a sheath) that also passes a core member therethrough that forms the core, or push rod of the delivery system. The core is slidably disposable with respect to the sheath. By advancing the core member with the prosthesis mounted thereto distally outwardly of the sheath, the prosthesis can self-expand, or be expanded by a balloon. However, if the tether is tensioned, it can cause the proximal end of the prosthesis to collapse radially inwardly such that the prosthesis can be withdrawn into the sheath. While adjacent undulating rings of the prosthesis particularly near the distal end of the prosthesis can be connected to each other (e.g., by sewing), they can also be kept independent of one another, and be attached to an inner and/or outer tubular fabric layer. The rigidity of the prosthesis is selected and/or configured to provide a desired performance. Thus, the distal end can be relatively rigid to maintain an opening in the wall of a vessel or other organ in an open state that the prosthesis traverses through by resisting the force of the vessel wall to want to "close" the hole in itself. The proximal region is less rigid and can accommodate increasing vessel curvature of the vessel that it is mounted in.

The devices and methods disclosed herein can be used for other procedures in an as-is condition, or can be modified as needed to suit the particular procedure. In view of the many possible embodiments to which the principles of this disclosure may be applied, it should be recognized that the illustrated embodiments are only preferred examples of the disclosure and should not be taken as limiting the scope of the disclosure.

What is claimed is:

1. A tubular prosthesis, comprising:
an elongate compliant tubular body having a proximal end and a distal end, the elongate compliant tubular body being formed at least in part from a plurality of undulating strut rings arranged axially along a central longitudinal axis of the tubular prosthesis, the central longitudinal axis defining an axial direction;
a distal sealing flange operably coupled to the distal end of the elongate compliant tubular body, the distal sealing flange being formed at least in part from a first undulating filament configured into a shape of a multi-pointed star having a first plurality of convex radially outwardly directed vertices separated by a second plurality of radially inwardly directed concave vertices, the distal sealing flange being configured and arranged to facilitate seating the tubular prosthesis against a first concave vessel wall of a first vessel, wherein the tubular prosthesis is configured to extend outwardly through an ostium formed in the first concave vessel wall when deployed, wherein the distal sealing flange remains inside the ostium after deployment; and
two opposing laterally extending projections operably coupled to the elongate compliant tubular body, the two opposing laterally extending projections being formed by two laterally extending loop portions formed from a second filament shaped into a distal strut ring structurally and physically distinct from the distal sealing flange having a first circumferential portion formed by a first set of undulations that lay in a cylindrical plane that surrounds the longitudinal axis and a second circumferential portion formed by a second set of undulations that also lay in the cylindrical plane, wherein the first circumferential portion and the second circumferential portion are joined to each other by the two laterally extending loop portions, wherein the distal strut ring is located along the axial direction between the distal sealing flange and a penultimate undulating strut ring of the plurality of undulating strut rings, wherein the two laterally extending loop sections extend radially outwardly to a width that is wider than a maximum lateral width of the distal sealing flange, the two laterally extending loop sections being configured to rest in a bottom of the first concave wall of the first vessel on either side of said ostium beyond an outward radial extent of the distal sealing flange to prevent the prosthesis from being pulled through said ostium after deployment.

2. The tubular prosthesis of claim 1, wherein a membrane covers the elongate compliant tubular body and the distal flange.

3. The tubular prosthesis of claim 2, wherein the membrane includes a woven or non-woven fabric.

4. The tubular prosthesis of claim 2, wherein the membrane includes an expanded polytetrafluoroethylene ("ePTFE") material.

5. The tubular prosthesis of claim 2, wherein the membrane includes a biological tissue material.

6. The tubular prosthesis of claim 2, wherein the laterally extending projections are not covered by the membrane.

7. The tubular prosthesis of claim 2, wherein each of the laterally extending projections includes at least one radiopaque marker formed thereon.

8. The tubular prosthesis of claim 7, wherein each of the laterally extending projections includes at least one of said radiopaque markers formed thereon at a location that resides at the ostium during implantation.

9. The tubular prosthesis of claim 7, wherein each of the laterally extending projections further includes at least one radiopaque marker formed near an outward lateral tip of each of the laterally extending projections, respectively.

10. The tubular prosthesis of claim 1, wherein the two laterally extending loop sections are circumferentially adjacent to respective radially inwardly directed concave vertices of the second plurality of radially inwardly directed concave vertices.

11. The tubular prosthesis of claim 1, wherein each of the two opposing laterally extending projections lay in a plane that is orthogonal with respect to the central longitudinal axis.

12. The tubular prosthesis of claim 1, wherein each of the two laterally extending loop sections comprises a closed loop.

13. The tubular prosthesis of claim 1, wherein each of the two laterally extending loop sections comprises an open "U"-shaped loop.

14. The tubular prosthesis of claim 1, further comprising:
a proximal sealing flange operably coupled to the proximal end of the elongate compliant tubular body, the proximal sealing flange being formed at least in part from a first proximal undulating filament configured into a shape of a multi-pointed star having a first plurality of convex radially outwardly directed vertices separated by a second plurality of radially inwardly directed concave vertices, the proximal sealing flange being configured and arranged to facilitate seating the tubular prosthesis against a second concave vessel wall of a second vessel, wherein the tubular prosthesis is configured to extend outwardly through a second ostium formed in the second concave vessel wall when deployed, wherein the proximal sealing flange remains inside the second ostium after deployment; and
two further opposing laterally extending projections operably coupled to the proximal end of the elongate compliant tubular body, the two further opposing laterally extending projections being formed by two further laterally extending loop portions formed from a second proximal filament shaped into a proximal strut ring structurally and physically distinct from the proximal sealing flange having a first circumferential portion formed by a first set of undulations that lay in the cylindrical plane that surrounds the longitudinal axis and a second circumferential portion formed by a second set of undulations that also lay in the cylindrical plane, wherein the first circumferential portion and the second circumferential portion are joined to each other by the-two further laterally extending loop sections, wherein the proximal strut ring is located along the axial direction between the proximal sealing flange and a proximal penultimate undulating strut ring of the plurality of undulating strut rings, wherein the two laterally extending loop sections extend radially outwardly to a width that is wider than a maximum lateral width of the distal sealing flange, the two further laterally extending loop portions being configured to rest in a bottom of the second concave wall of the second vessel on either side of said second ostium beyond an outward radial extent of the proximal sealing flange to prevent the prosthesis from being pulled through said second ostium after deployment.

* * * * *